United States Patent
Tsugita et al.

(12)

(10) Patent No.: US 6,371,971 B1
(45) Date of Patent: Apr. 16, 2002

(54) GUIDEWIRE FILTER AND METHODS OF USE

(75) Inventors: Ross Tsugita; Jean Chang, both of Mountain View, CA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/560,360

(22) Filed: Apr. 28, 2000

Related U.S. Application Data

(63) Continuation of application No. 09/440,204, filed on Nov. 15, 1999.

(51) Int. Cl.[7] .............................................. A61M 29/00
(52) U.S. Cl. ...................................................... 606/200
(58) Field of Search ................................ 606/200, 191, 606/192, 194, 198, 108, 159; 604/27, 28, 106, 107, 108, 109

(56) References Cited

U.S. PATENT DOCUMENTS

| 3,472,230 A | 10/1969 | Fogarty | 128/328 |
| 3,592,186 A | 7/1971 | Oster | 128/2 R |

(List continued on next page.)

FOREIGN PATENT DOCUMENTS

| DE | 28 21 048 | 7/1980 | A61B/17/22 |
| DE | 34 17 738 | 11/1985 | A61M/1/34 |
| DE | 40 30 998 A1 | 10/1990 | A61F/2/01 |
| EP | 0 200 688 | 11/1986 | A61B/17/22 |
| EP | 0 293 605 A1 | 12/1988 | A61F/2/02 |
| EP | 0 411 118 A1 | 2/1991 | A61M/25/00 |
| EP | 0 427 429 A2 | 5/1991 | A61M/25/10 |
| EP | 0 437 121 B1 | 7/1991 | A61F/2/02 |
| EP | 0 472 334 A1 | 2/1992 | A61F/2/02 |
| EP | 0 472 368 A2 | 2/1992 | A61B/17/22 |
| EP | 0533511 | 3/1993 | |
| EP | 0 533 511 A1 | 3/1993 | A61M/29/02 |
| EP | 0 655 228 A1 | 11/1994 | A61F/2/02 |

(List continued on next page.)

OTHER PUBLICATIONS

"Atherosclerotic Disease of the Aortic Arch as a Risk Factor of Recurrent Ischemic Stroke," *The New England Journal of Medicine*, pp. 1216–1221 (May 1996).

"Endovascular Grafts, Stents Drive Interventional Radiology growth," *Cardiovascular Device Update*, 2(3):1–12 (Mar. 1996).

(List continued on next page.)

*Primary Examiner*—Henry J. Recla
*Assistant Examiner*—Vy Q. Bui
(74) *Attorney, Agent, or Firm*—Crompton, Seager & Tufte LLC

(57) ABSTRACT

A filter system for temporary placement of a filter in an artery or vein is disclosed. The filter system includes a guidewire that is first positioned across a lesion within a vessel. The guidewire may include a distal stop. A slideable filter is then advanced along the guidewire using an advancing mechanism, typically an elongate member slideable over the guidewire and contacting the filter. A capture sheath may be disposed about the filter during advancement. Once the filter is positioned downstream of the lesion, the capture sheath is withdrawn, allowing the filter to expand. Further distal advancement of the filter is prohibited by the stop. After expansion of the filter, the capture sheath and the advancing mechanism are withdrawn from the region of interest, and removed from the patient's vessel. The filter may then be retrieved using a capture sheath or exchanged for a second filter after removing the first filter.

10 Claims, 15 Drawing Sheets

U.S. PATENT DOCUMENTS

| | | | |
|---|---|---|---|
| 3,683,904 A | 8/1972 | Forster | 128/127 |
| 3,889,657 A | 6/1975 | Baumgarten | 128/2 |
| 3,952,747 A | 4/1976 | Kimmell, Jr. | 128/303 R |
| 3,996,938 A | 12/1976 | Clark, III | 128/348 |
| 4,046,150 A | 9/1977 | Schwartz et al. | 128/328 |
| 4,425,908 A | 1/1984 | Simon | 128/1 |
| 4,447,227 A | 5/1984 | Kotsanis | 604/95 |
| 4,580,568 A | 4/1986 | Gianturco | 128/345 |
| 4,590,938 A | 5/1986 | Segura et al. | 128/328 |
| 4,619,246 A | 10/1986 | Molgaard-Nielsen et al. | 128/1 |
| 4,631,052 A | 12/1986 | Kensey | 604/22 |
| 4,643,184 A | 2/1987 | Mobin-Uddin | 128/303 |
| 4,650,466 A | 3/1987 | Luther | 604/95 |
| 4,662,885 A | 5/1987 | DiPisa, Jr. | 623/1 |
| 4,705,517 A | 11/1987 | DiPisa, Jr. | 623/12 |
| 4,706,671 A | 11/1987 | Weinrib | 128/348.1 |
| 4,723,549 A | 2/1988 | Wholey | 128/344 |
| 4,728,319 A | 3/1988 | Masch | 604/22 |
| 4,733,665 A | 3/1988 | Palmaz | 128/343 |
| 4,790,812 A | 12/1988 | Hawkins, Jr. et al. | 604/22 |
| 4,790,813 A | 12/1988 | Kensey | 604/22 |
| 4,794,928 A | 1/1989 | Kletschka | 128/344 |
| 4,794,931 A | 1/1989 | Yock | 128/660.03 |
| 4,800,882 A | 1/1989 | Gianturco | 128/343 |
| 4,807,626 A | 2/1989 | McGirr | 128/328 |
| 4,842,579 A | 6/1989 | Shiber | 606/22 |
| 4,857,045 A | 8/1989 | Rydell | 604/22 |
| 4,857,046 A | 8/1989 | Stevens et al. | 604/22 |
| 4,867,157 A | 9/1989 | McGurk-Burleson et al. | 128/305 |
| 4,873,978 A | 10/1989 | Ginsburg | 128/345 |
| 4,898,575 A | 2/1990 | Fischell et al. | 604/12 |
| 4,907,336 A | 3/1990 | Gianturco | 29/515 |
| 4,921,478 A | 5/1990 | Solano et al. | 604/53 |
| 4,921,484 A | 5/1990 | Hillstead | 604/104 |
| 4,926,858 A | 5/1990 | Giffort, III et al. | 606/159 |
| 4,950,277 A | 8/1990 | Farr | 606/159 |
| 4,955,895 A | 9/1990 | Sugiyama et al. | 606/194 |
| 4,957,482 A | 9/1990 | Shiber | 604/22 |
| 4,969,891 A | 11/1990 | Gewertz | 606/200 |
| 4,979,951 A | 12/1990 | Simpson | 606/159 |
| 4,986,807 A | 1/1991 | Farr | 604/22 |
| 4,998,539 A | 3/1991 | Delsanti | 128/898 |
| 5,002,560 A | 3/1991 | Machold et al. | 606/198 |
| RE33,569 E | 4/1991 | Gifford, III et al. | 606/159 |
| 5,007,896 A | 4/1991 | Shiber | 604/170 |
| 5,007,917 A | 4/1991 | Evans | 606/170 |
| 5,011,488 A | 4/1991 | Ginsburg | 606/159 |
| 5,019,088 A | 5/1991 | Farr | 606/159 |
| 5,041,126 A | 8/1991 | Gianturco | 606/195 |
| 5,053,008 A | 10/1991 | Bajaj | 604/104 |
| 5,053,044 A | 10/1991 | Mueller et al. | 606/159 |
| 5,071,407 A | 12/1991 | Termin et al. | 604/104 |
| 5,071,425 A | 12/1991 | Gifford, III et al. | 606/159 |
| 5,085,662 A | 2/1992 | Willard | 606/159 |
| 5,087,265 A | 2/1992 | Summers | 606/159 |
| 5,100,423 A | 3/1992 | Fearnot | 606/15 |
| 5,100,424 A | 3/1992 | Jang et al. | 606/159 |
| 5,100,425 A | 3/1992 | Fischell et al. | 606/159 |
| 5,102,415 A | 4/1992 | Guenther et al. | 606/159 |
| 5,104,399 A | 4/1992 | Lazarus | 623/1 |
| 5,108,419 A | 4/1992 | Reger et al. | 606/200 |
| 5,133,733 A | 7/1992 | Rasmussen et al. | 606/200 |
| 5,135,531 A | 8/1992 | Shiber | 606/159 |
| 5,152,771 A | 10/1992 | Sabbaghian et al. | 606/159 |
| 5,152,777 A | 10/1992 | Goldberg et al. | 606/200 |
| 5,160,342 A | 11/1992 | Reger et al. | 606/200 |
| 5,171,233 A | 12/1992 | Amplatz et al. | 604/281 |
| 5,190,546 A | 3/1993 | Jervis | 606/78 |
| 5,195,955 A | 3/1993 | Don Michael | 604/22 |
| 5,224,953 A | 7/1993 | Morgentaler | 606/192 |
| 5,306,286 A | 4/1994 | Stack et al. | 606/198 |
| 5,314,444 A | 5/1994 | Gianturco | 606/195 |
| 5,314,472 A | 5/1994 | Fontaine | 623/12 |
| 5,318,576 A | 6/1994 | Plassche, Jr. et al. | 606/159 |
| 5,329,942 A | 7/1994 | Gunther et al. | 128/898 |
| 5,330,484 A | 7/1994 | Günther et al. | 606/128 |
| 5,330,500 A | 7/1994 | Song | 606/198 |
| 5,350,398 A | 9/1994 | Pavcnik et al. | 606/200 |
| 5,354,310 A | 10/1994 | Garnic et al. | 606/198 |
| 5,356,423 A | 10/1994 | Tihon et al. | 606/194 |
| 5,366,464 A | 11/1994 | Belknap | 606/159 |
| 5,366,473 A | 11/1994 | Winston et al. | 606/198 |
| 5,370,657 A | 12/1994 | Irie | 606/200 |
| 5,370,683 A | 12/1994 | Fontaine | 623/1 |
| 5,376,100 A | 12/1994 | Lefebvre | 606/180 |
| 5,383,887 A | 1/1995 | Nadal | 606/200 |
| 5,383,892 A | 1/1995 | Cardon et al. | 606/198 |
| 5,383,926 A | 1/1995 | Lock et al. | 623/1 |
| 5,387,235 A | 2/1995 | Chuter | 623/1 |
| 5,395,349 A | 3/1995 | Quiachon et al. | 604/248 |
| 5,397,345 A | 3/1995 | Lazerus | 623/1 |
| 5,405,377 A | 4/1995 | Cragg | 623/1 |
| 5,409,454 A | 4/1995 | Fischell et al. | 604/22 |
| 5,415,630 A | 5/1995 | Gory et al. | 604/53 |
| 5,419,774 A | 5/1995 | Willard et al. | 604/22 |
| 5,421,832 A | 6/1995 | Lefebvre | 604/53 |
| 5,423,742 A | 6/1995 | Theron | 604/28 |
| 5,423,885 A | 6/1995 | Williams | 623/1 |
| 5,425,765 A | 6/1995 | Tiefenbrun et al. | 623/12 |
| 5,443,498 A | 8/1995 | Fontaine | 623/1 |
| 5,449,372 A | 9/1995 | Schmaltz et al. | 606/198 |
| 5,456,667 A | 10/1995 | Ham et al. | 604/107 |
| 5,462,529 A | 10/1995 | Simpson et al. | 604/101 |
| 5,476,104 A | 12/1995 | Sheahon | 128/757 |
| 5,484,418 A | 1/1996 | Quiachon et al. | 604/167 |
| 5,507,767 A | 4/1996 | Maeda et al. | 606/198 |
| 5,512,044 A | 4/1996 | Duer | 604/22 |
| 5,527,354 A | 6/1996 | Fontaine et al. | 623/1 |
| 5,536,242 A | 7/1996 | Willard et al. | 604/30 |
| 5,540,707 A | 7/1996 | Ressemann et al. | 606/159 |
| 5,549,626 A | 8/1996 | Miller et al. | 606/200 |
| 5,562,724 A | 10/1996 | Vowerk et al. | 623/1 |
| 5,569,274 A | 10/1996 | Rapacki et al. | 606/158 |
| 5,569,275 A | 10/1996 | Kotula et al. | 606/159 |
| 5,634,897 A | 6/1997 | Dance et al. | 604/35 |
| 5,658,296 A | 8/1997 | Bates et al. | 606/127 |
| 5,662,671 A | 9/1997 | Barbut et al. | 606/170 |
| 5,669,933 A | 9/1997 | Simon et al. | 600/200 |
| 5,695,519 A | 12/1997 | Summers | 606/200 |
| 5,709,704 A | 1/1998 | Nott et al. | 606/200 |
| 5,720,764 A | 2/1998 | Naderlinger | 606/200 |
| 5,728,066 A | 3/1998 | Daneshvar | 604/96 |
| 5,746,758 A | 5/1998 | Nordgren et al. | 606/159 |
| 5,749,848 A | 5/1998 | Jang et al. | 604/53 |
| 5,769,816 A | 6/1998 | Barbut et al. | 604/96 |
| 5,779,716 A | 7/1998 | Cano et al. | 606/114 |
| 5,792,300 A | 8/1998 | Inderbitzen et al. | 156/244.13 |
| 5,795,322 A | 8/1998 | Boudewijm | 604/22 |
| 5,797,952 A | 8/1998 | Klein | 606/198 |
| 5,800,457 A | 9/1998 | Gelbfish | 606/200 |
| 5,800,525 A | 9/1998 | Bachinski et al. | 623/1 |
| 5,810,874 A | 9/1998 | Lefebvre | 606/200 |
| 5,814,064 A | 9/1998 | Daniel | 606/200 |
| 5,817,102 A | 10/1998 | Johnson et al. | 606/108 |
| 5,827,324 A | 10/1998 | Cassell et al. | 606/200 |
| 5,833,644 A | 11/1998 | Zado-Azizi et al. | 604/52 |
| 5,833,650 A | 11/1998 | Imran | 604/53 |
| 5,846,260 A | 12/1998 | Maahs | 606/200 |
| 5,848,964 A | 12/1998 | Samuels | 600/200 |
| 5,876,367 A | 3/1999 | Kaganov et al. | 604/8 |

| Patent No. | Date | Inventor | Class |
|---|---|---|---|
| 5,893,867 A | 4/1999 | Bagaoisan et al. | 606/198 |
| 5,895,399 A | 4/1999 | Barbut et al. | 606/159 |
| 5,902,263 A | 5/1999 | Patterson et al. | 604/22 |
| 5,906,618 A | 5/1999 | Larson, III | 606/108 |
| 5,908,435 A | 6/1999 | Samuels | 606/200 |
| 5,910,154 A | 6/1999 | Tsugita et al. | 606/200 |
| 5,911,734 A | 6/1999 | Tsugita et al. | 606/200 |
| 5,916,193 A | 6/1999 | Stevens et al. | 604/53 |
| 5,925,016 A | 7/1999 | Chornenky et al. | 604/96 |
| 5,925,060 A | 7/1999 | Forber | 606/191 |
| 5,925,062 A | 7/1999 | Purdy | 606/200 |
| 5,925,063 A | 7/1999 | Khosravi | 606/200 |
| 5,928,203 A | 7/1999 | Davey et al. | 604/247 |
| 5,928,218 A | 7/1999 | Gelbfish | 604/540 |
| 5,934,284 A | 8/1999 | Plaia et al. | 128/898 |
| 5,935,139 A | 8/1999 | Bates | 606/159 |
| 5,938,645 A | 8/1999 | Gordon | 604/264 |
| 5,941,869 A | 8/1999 | Patterson et al. | 604/508 |
| 5,941,896 A | 8/1999 | Kerr | 606/200 |
| 5,947,995 A | 9/1999 | Samuels | 606/200 |
| 5,951,585 A | 9/1999 | Cathcart et al. | 606/200 |
| 5,954,745 A | 9/1999 | Gertler et al. | 606/200 |
| 5,976,172 A | 11/1999 | Homsma | 606/200 |
| 5,989,210 A | 11/1999 | Morris et al. | 604/22 |
| 5,989,271 A | 11/1999 | Bonnette et al. | 606/159 |
| 5,989,281 A | 11/1999 | Barbut et al. | 606/200 |
| 5,993,469 A | 11/1999 | McKenzie et al. | 606/159 |
| 5,997,557 A | 12/1999 | Barbut et al. | 606/159 |
| 6,001,118 A | 12/1999 | Daniel | 606/200 |
| 6,007,557 A | 12/1999 | Ambrisco et al. | 606/200 |
| 6,010,522 A | 1/2000 | Barbut et al. | 606/200 |
| 6,013,085 A | 1/2000 | Howard | 606/108 |
| 6,027,520 A | 2/2000 | Tsugita et al. | 606/200 |
| 6,051,014 A | 4/2000 | Jang | 606/200 |
| 6,053,932 A | 4/2000 | Daniel et al. | 606/200 |
| 6,059,814 A | 5/2000 | Ladd | 606/200 |
| 6,068,645 A | 5/2000 | Tu | 606/200 |
| 6,086,605 A | 7/2000 | Barbut et al. | 606/200 |
| 6,129,739 A | 10/2000 | Khosravi | 606/200 |
| 6,142,987 A | 11/2000 | Tsugita | 604/500 |
| 6,152,946 A | 11/2000 | Broome et al. | 606/200 |
| 6,165,200 A | 12/2000 | Tugita et al. | 606/200 |
| 6,168,579 B1 | 1/2001 | Tsugita | 604/96.01 |
| 6,171,327 B1 | 1/2001 | Daniel et al. | 606/200 |
| 6,179,851 B1 | 1/2001 | Barbut et al. | 606/159 |
| 6,179,859 B1 * | 1/2001 | Bates et al. | 606/200 |
| 6,179,861 B1 | 1/2001 | Khosravi et al. | 606/200 |
| 6,203,561 B1 | 3/2001 | Ramee et al. | 606/200 |
| 6,214,026 B1 | 4/2001 | Lepak et al. | 606/200 |

FOREIGN PATENT DOCUMENTS

| | | | |
|---|---|---|---|
| EP | 0 686 379 A2 | 6/1995 | A61F/2/06 |
| EP | 0 696 447 A2 | 2/1996 | A61F/2/06 |
| EP | 0 737 450 A1 | 10/1996 | A61F/2/01 |
| EP | 0 759 287 A1 | 2/1997 | A61F/2/01 |
| EP | 0 771 549 A2 | 5/1997 | A61F/2/01 |
| EP | 0 784 988 A1 | 7/1997 | A61M/5/165 |
| EP | 0 852 132 A1 | 7/1998 | A61F/2/01 |
| EP | 0 934 729 | 8/1999 | |
| EP | 0968688 | 1/2000 | |
| FR | 2 580 504 | 10/1986 | A61M/1/00 |
| FR | 2 643 250 A1 | 8/1990 | A61B/17/00 |
| FR | 2 666 980 | 3/1992 | A61F/2/02 |
| FR | 2 768 326 A1 | 3/1999 | A61F/2/01 |
| GB | 2 020 557 B | 1/1993 | A61B/17/50 |
| JP | 8-187294 A | 7/1996 | A61M/29/00 |
| SU | 764684 | 9/1980 | A61M/25/00 |
| WO | WO 92/03097 | 3/1992 | A61B/17/00 |
| WO | WO 94/14389 | 7/1994 | A61F/2/02 |
| WO | WO 94/24946 | 11/1994 | A61B/17/22 |
| WO | WO96/01591 | 1/1996 | |
| WO | WO 96/01591 | 1/1996 | A61B/17/22 |
| WO | WO 96/10375 | 4/1996 | A61F/2/06 |
| WO | WO 96/19941 | 7/1996 | A61B/17/00 |
| WO | WO96/23441 | 8/1996 | |
| WO | WO 96/23441 | 8/1996 | A61B/5/00 |
| WO | WO 96/33677 | 10/1996 | A61F/11/00 |
| WO | 0 743 046 A1 | 11/1996 | A61F/2/01 |
| WO | WO 97/17100 | 5/1997 | A61M/29/00 |
| WO | WO 97/27808 | 8/1997 | A61B/17/22 |
| WO | WO 97/42879 | 11/1997 | A61B/17/00 |
| WO | WO 98/02084 | 1/1998 | |
| WO | WO 98/02112 | 1/1998 | A61F/2/01 |
| WO | WO 98/23322 | 6/1998 | A61M/29/00 |
| WO | WO 98/33443 | 8/1998 | A61B/17/22 |
| WO | WO98/33443 | 8/1998 | |
| WO | WO 98/34673 | 8/1998 | A61M/31/00 |
| WO | WO 98/36786 | 8/1998 | A61M/5/32 |
| WO | WO 98/38920 | 9/1998 | A61B/17/00 |
| WO | WO 98/38929 | 9/1998 | A61B/17/22 |
| WO | WO 98/39046 | 9/1998 | A61M/25/00 |
| WO | WO 98/39053 | 9/1998 | A61M/29/00 |
| WO | WO 98/46297 | 10/1998 | A61M/29/00 |
| WO | WO 98/47447 | 10/1998 | A61F/2/06 |
| WO | WO 98/49952 | 11/1998 | A61B/17/32 |
| WO | WO 98/50103 | 11/1998 | A61M/29/00 |
| WO | WO 98/51237 | 11/1998 | A61F/2/01 |
| WO | WO 98/55175 | 12/1998 | A61M/29/00 |
| WO | WO 99/09895 | 3/1999 | A61B/17/12 |
| WO | WO 99/22673 | 5/1999 | A61F/2/01 |
| WO | WO99/22673 | 5/1999 | |
| WO | WO 99/23976 | 5/1999 | A61F/2/01 |
| WO | WO99/23976 | 5/1999 | |
| WO | WO 99/25252 | 5/1999 | A61B/17/00 |
| WO | WO99/25252 | 5/1999 | |
| WO | WO 99/30766 | 6/1999 | A61M/29/00 |
| WO | WO 99/40964 | 8/1999 | A61M/29/02 |
| WO | WO 99/42059 | 8/1999 | A61F/2/06 |
| WO | WO 99/44510 | 9/1999 | A61B/17/00 |
| WO | WO 99/44542 | 9/1999 | A61B/2/06 |
| WO | WO99/49808 | 10/1999 | |
| WO | WO99/51166 | 10/1999 | |
| WO | WO 99/55236 | 11/1999 | A61B/17/00 |
| WO | WO 99/58068 | 11/1999 | A61B/17/22 |
| WO | WO 00/07655 | 2/2000 | A61M/29/00 |
| WO | WO 00/09054 | 2/2000 | A61F/7/12 |
| WO | WO 00/16705 | 3/2000 | A61B/17/22 |
| WO | WO 00/49970 | 8/2000 | A61F/2/01 |

OTHER PUBLICATIONS

"Protruding Atheromas in the Thoracic Aortic and Systemic Embolization." pp. 423–427 American College of Physicians (1991).

"Recognition and Embolic Potential of Intraaortic Atherosclerotic Debris," American College of Cardiology (Jan. 1991).

Cragg, Andrew et al., "A New Percutaneous Vena Cava Filger," *AJR, 141*:601–604 (Sep. 1983).

Cragg, Andrew et al., "Nonsurgical Placement of Arterial Endoprosthesis: A New Technique Using Nitrino Wire," *AJR*, pp. 261–263 (Apr. 1983).

Diethrich et al., "Percutaneous Techniques for Endoluminal Carotid Interventions," *J. Endovasc. Surg., 3*:182–202 (1996).

Fadali, A. Moneim, "A filtering device for the prevention of particulate embolization during the course of cardiac surgery," *Surgery, 64*(3):634–639 (Sep 1968).

Haissaguerre et al., "Spontaneous Initiation of Atrial Fibrillation by Ectopic Beats Originating in the Pulmonary Veins," *The New England Journal of Medicine, 333*(10):659–666 (Sep. 1988).

Jordan, Jr. et al., "Microemboli Detected by Transcranial Doppler Monitoring . . . , " *Cardiovascular Surgery, 7*(1)33–38 (Jan. 1999).

Lesh, "Can Catheter Ablation Cure Atrial Fibrillation" *ACC Current Journal Review,* pp. 38–40 (Sep./Oct. 1997).

Lund, et al., "Long–Term Patentcy of Ductus Arteriosus After Balloon Dilation: an Experimental Study," *Laboratory Investigation, 64*(4):772–774 (Apr. 1984).

Marache et al., "Percutaneous Transluminal Venous Angioplasty . . . ," *American Heart Journal,* 125(2Pt 1):362–366 (Feb. 1993).

Mazur et al., "Directional Atherectomy with the Omnicath™: A Unique New Catheter System," *Catheterization and Cardiovascular Diagnosis, 31*:17–84 (1994).

Moussa, MD, Issaam "Stents Don't Require Systemic Anticoagulation . . . But the Technique (and Results) Must be Optimal," *Journal of Invasive Cardiol., 8*(E):3E–7E, (1996).

Nakanishi et al., "Catheter Intervention to Venous System Using Exandable Metallic Stents," *Rinsho Kyobu Geka, 13*(2):English Abstract Only (Apr. 1994).

Onal et al., "Primary Stenting for Complex Atherosclerotic Plaques in Aortic and Iliac Stenoses," *Cardiovascular & Interventional Radiology, 21*(5):386–392 (1998).

Theron et al., "New Triple Coaxial Catheter System for Carotid Angioplasty with Cerebral Protection," *American Journal of Neuroradiology, 11*:869–874 (1990).

Tunick et al., "Protruding atherosclerotic plaque in the aortic archo f patients with systemic embolization: A new finding seen by transesophageal echocardiography," *American Heart Journal 120*(3):658–660 (Sep. 1990).

Waksman et al., "Distal Embolization is Common After Directional Atherectomy . . . ," *American Heart Journal, 129*(3):430–435 (1995).

Wholey, Mark H. et al., PTA and Stents in the Treatment of Extracranial Circulation, *The Journal of Invasive Cardiology, 8*(E):25E–30E (1996).

* cited by examiner

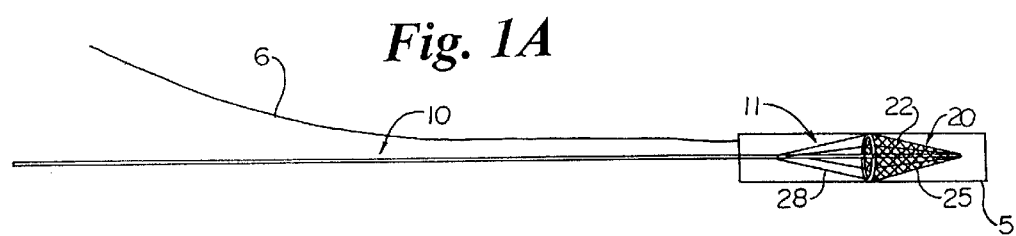
*Fig. 1A*
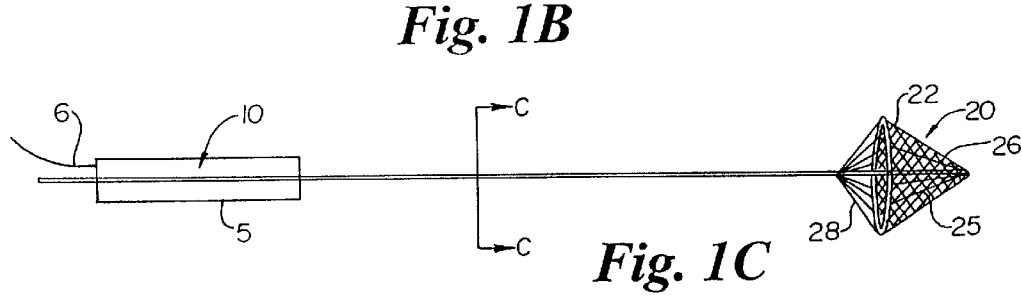
*Fig. 1B*
*Fig. 1C*
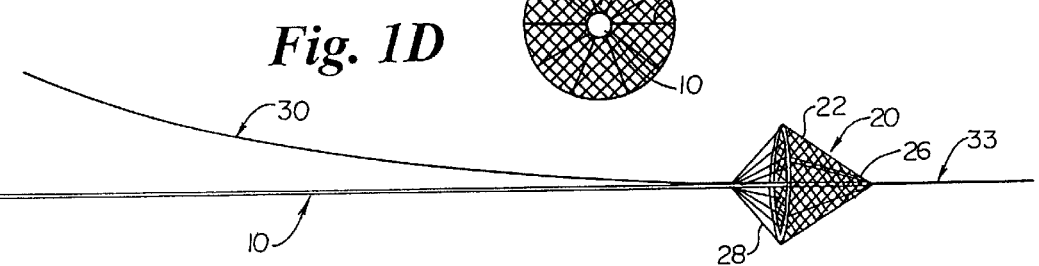
*Fig. 1D*

*Fig. 2A*     *Fig. 2B*     *Fig. 2C*
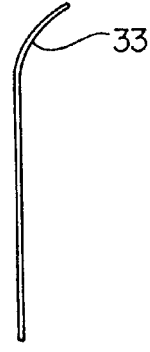
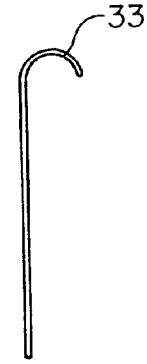
*Fig. 3A*
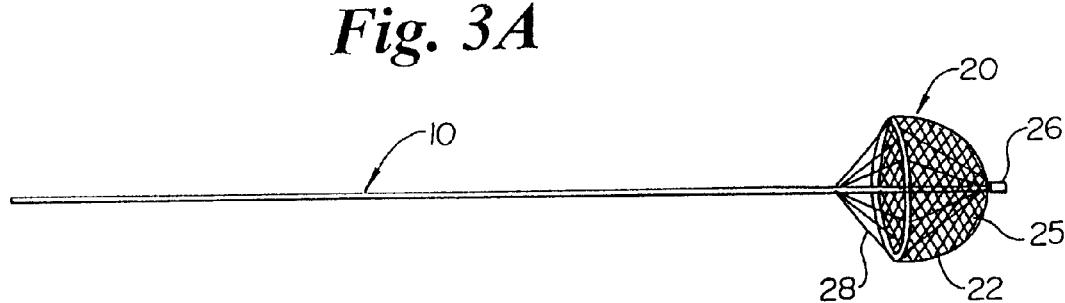
*Fig. 3B*
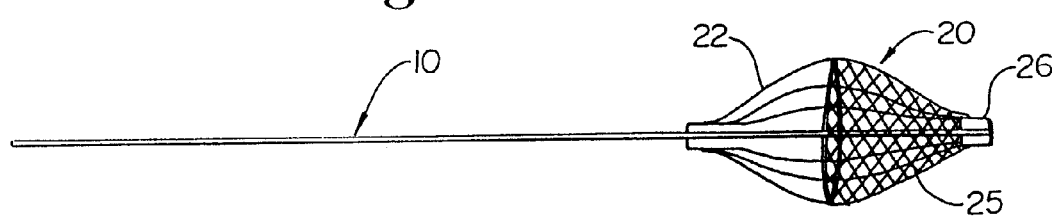

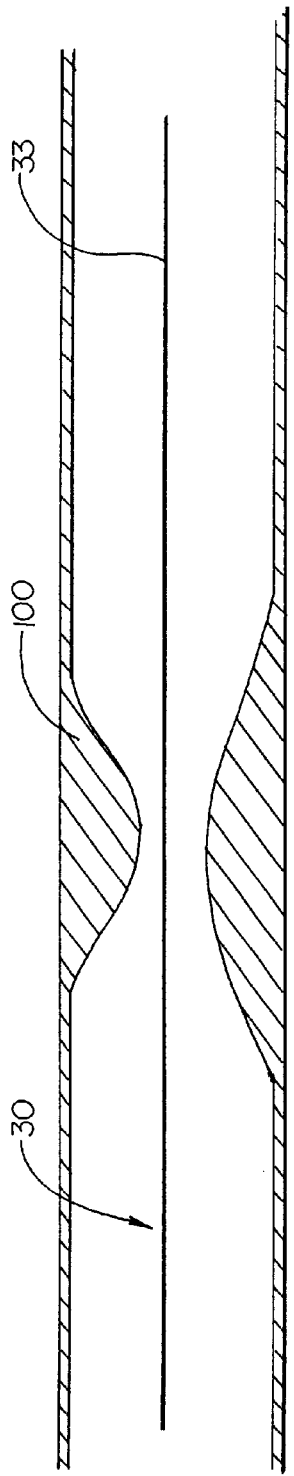
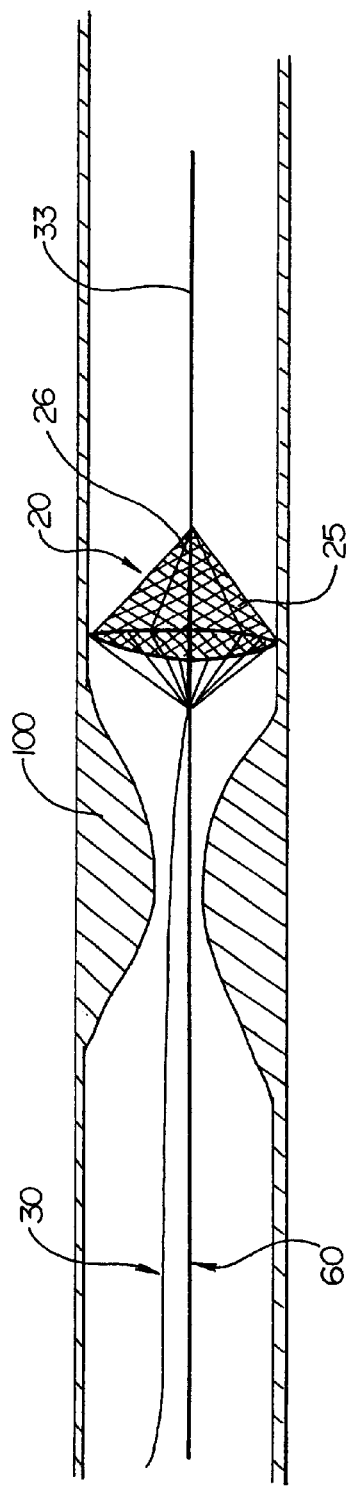
Fig. 4A
Fig. 4B

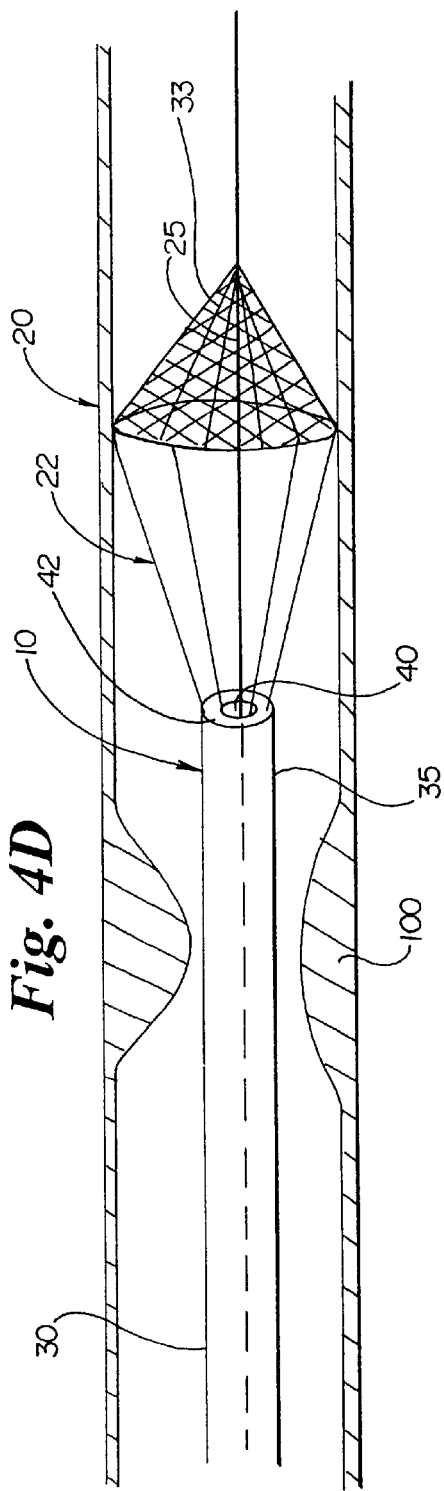
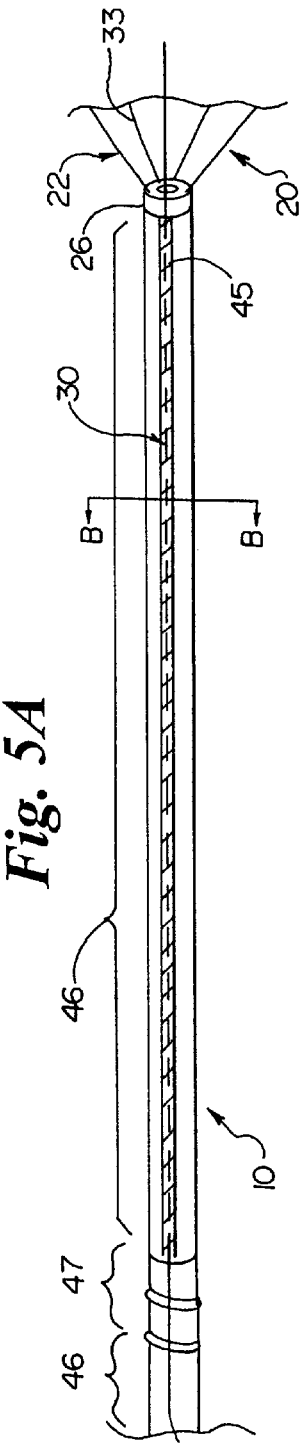
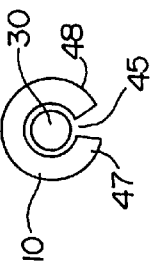
Fig. 4D
Fig. 5A
Fig. 5B

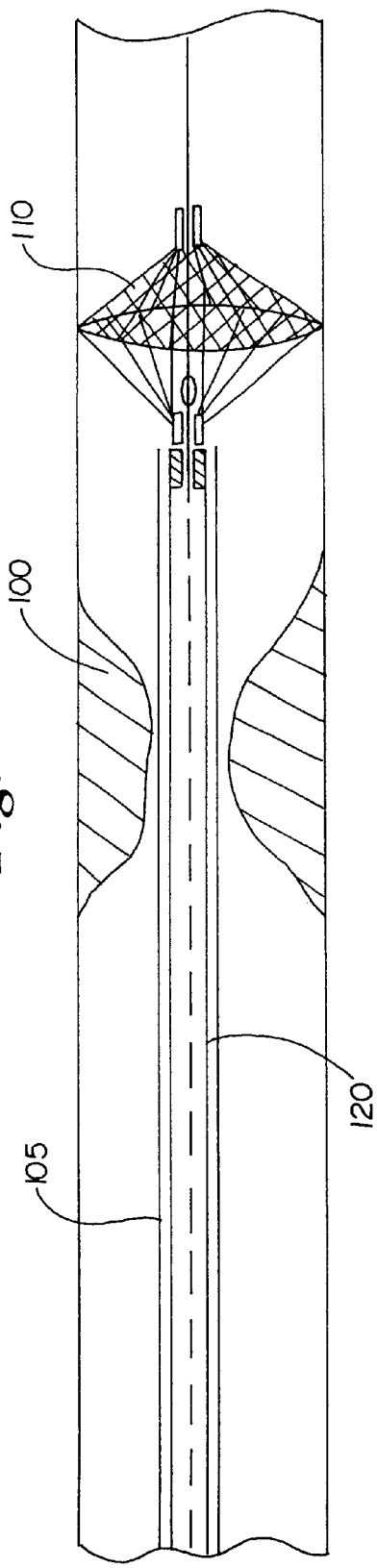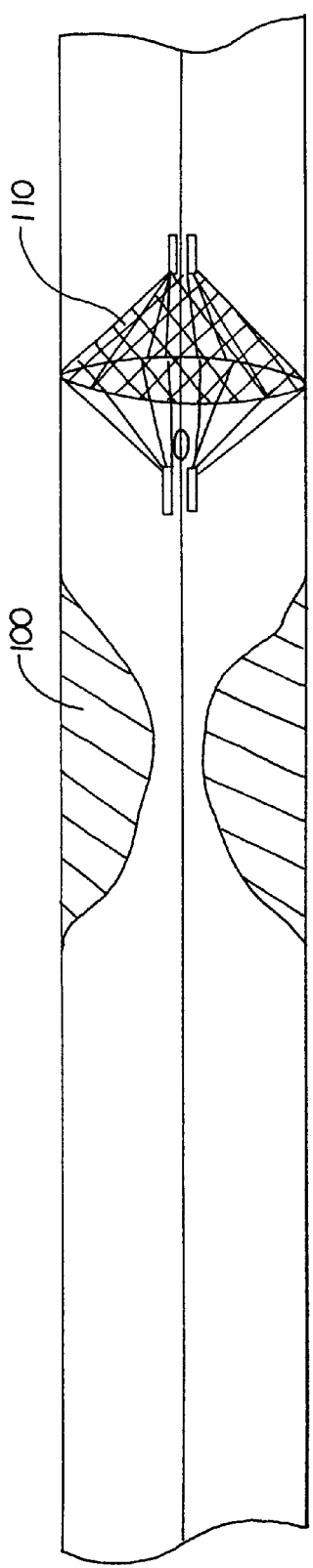

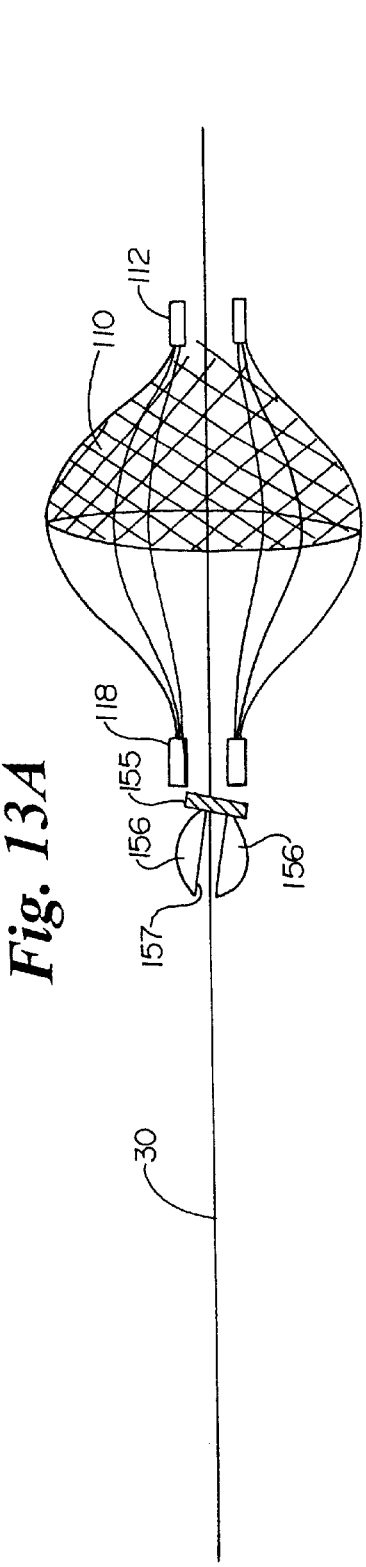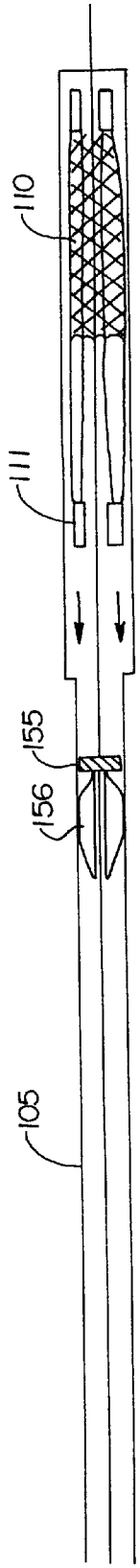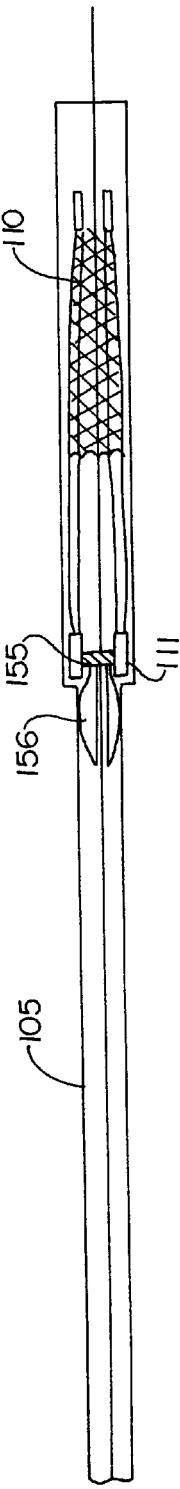

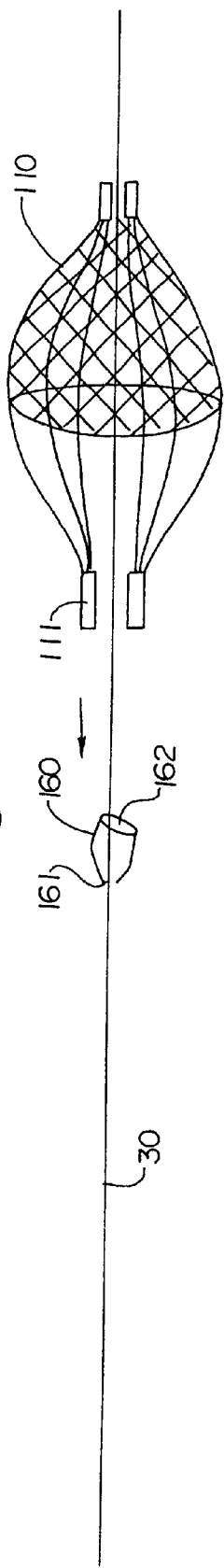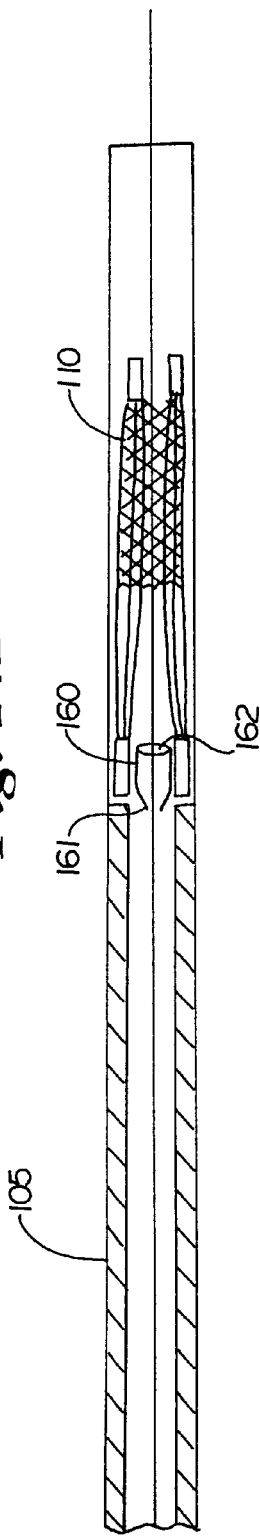
Fig. 14A
Fig. 14B

GUIDEWIRE FILTER AND METHODS OF USE

This is a continuation of U.S. application Ser. No. 09/440,204, filed Nov. 15, 1999, which is expressly incorporated herein by reference in its entirety.

FIELD OF THE INVENTION

The present invention relates generally to devices and methods for providing temporary placement of a filter in a blood vessel. More particularly, the invention provides a filter cartridge system for entrapment of embolic material in an artery or vein during an endovascular procedure. The system permits the replacement of the filter cartridge without requiring the removal of the guidewire during the endovascular procedure.

BACKGROUND OF THE INVENTION

Treatment of thrombotic or atherosclerotic lesions in blood vessels using an endovascular approach has recently proven to be an effective and reliable alternative to surgical intervention in selected patients. For example, directional atherectomy and percutaneous translumenal coronary angioplasty (PTCA) with or without stent deployment are useful in treating patients with coronary occlusion. Atherectomy physically removes plaque by cutting, pulverizing, or shaving in atherosclerotic arteries using a catheter-deliverable endarterectomy device. Angioplasty enlarges the diameter of a stenotic vessel by exerting mechanical force on the vascular walls. In addition to using angioplasty, stenting, and/or atherectomy on the coronary vasculature, these endovascular techniques have also proven useful in treating other vascular lesions in, for example, carotid artery stenosis, peripheral arterial occlusive disease (especially the aorta, the iliac artery, and the femoral artery), renal artery stenosis caused by atherosclerosis or fibromuscular disease, superior vena cava syndrome, and occlusive iliac vein thrombosis resistant to thrombolysis.

It is well recognized that one of the complications associated with endovascular techniques is the dislodgment of embolic materials generated during manipulation of the vessel, thereby causing occlusion of the narrower vessels downstream and ischemia or infarct of the organ that the vessel supplies. In 1995, Waksman et al. disclosed that distal embolization is common after directional atherectomy in coronary arteries and saphenous vein grafts. See Waksman et al., *American Heart Journal* 129(3): 430–5 (1995), (this and all other references cited herein are expressly incorporated by reference as if fully set forth in their entirety herein). This study found that distal embolization occurs in 28% (31 out of 11) of the patients undergoing atherectomy. In Jan. 1999, Jordan, Jr. et al. disclosed that treatment of carotid stenosis using percutaneous angioplasty with stenting is associated with more than eight times the rate of microemboli seen using carotid endarterectomy. See Jordan, Jr. et al. *Cardiovascular Surgery* 7(1): 33–8 (1999), incorporated herein by reference. Microemboli, as detected by transcranial Doppler monitoring in this study, have been shown to be a potential cause of stroke. The embolic materials include calcium, intimal debris, atheromatous plaque, thrombi, and/or air.

There are a number of devices designed to provide blood filtering for entrapment of vascular emboli. The vast majority of these devices are designed for permanent placement in veins to prevent pulmonary embolism. A temporary venous filter device is disclosed in Bajaj, U.S. Pat. No. 5,053,008, incorporated herein by reference. The Bajaj device is an intracardiac catheter for temporary placement in the pulmonary trunk of a patient predisposed to pulmonary embolism due to, e.g., hip surgery, major trauma, major abdominal or pelvic surgery, or immobilization. The Bajaj device includes an umbrella made from meshwork that traps venous emboli before they reach the lungs. This device is designed for venous filtration and is not suitable for arterial use because of the hemodynamic differences between arteries and veins.

There are very few intravascular devices designed for arterial use. Arteries are much more flexible and elastic than veins and, in the arteries, blood flow is pulsatile with large pressure variations between systolic and diastolic flow. These pressure variations cause the artery walls to expand and contract. Blood flow rates in the arteries vary from about 0.1 to 5 L/min. Ginsburg, U.S. Pat. No. 4,873,978, discloses an arterial filtering system, which includes a catheter with a strainer device at its distal end. This device is inserted into the vessel downstream from the treatment site and, after treatment, the strainer is collapsed around the entrapped emboli and removed from the body. The Ginsburg device, however, is integral with the catheter, unlike the devices described later herein. Ing. Walter Hengst GmbH & Co, German Patent DE 34 17 738, discloses another arterial filter having a folding linkage system that converts the filter from the collapsed to the expanded state.

Filters mounted to the distal end of guidewires have been proposed for intravascular blood filtration. A majority of these devices include a filter that is attached to a guidewire and is mechanically actuated via struts or a pre-shaped basket that deploys in the vessel. These filters are typically mesh "parachutes" that are attached to the shaft of the wire at the distal end and to wire struts that extend outward in a radial direction at their proximal end. The radial struts open the proximal end of the filter to the wall of the vessel. Blood flowing through the vessel is forced through the mesh thereby capturing embolic material in the filter.

Gilson et al., International Publication No. WO 99/23976 describes a guidewire with a filter slideably mounted thereon. Although the filter is not fixed to the guidewire at a single point, the filter is limited in its range of movement by two stops at the distal end of the guidewire, the stops being relatively closely spaced. Thus, unlike the present invention, in Gilson et al. the filter cannot be removed unless the entire guidewire is removed.

The useful in vivo time of a guidewire filter will vary, depending upon the type of procedure, the patient, and the blood flow. These factors may contribute to relatively short use time because of, for example, blood coagulation or excessive emboli clogging the filter mesh. Because for existing devices, the guidewire and the filter are integrated into one inseparable device, changing the filter after its useful in vivo deployment time has been completed requires the removal and replacement of the guidewire. This change requires time consuming and costly fluoroscopic guidance to reposition the new guidewire and filter.

There is a need in the art for a device that will not require removal and replacement of the guidewire should the in vivo useful life of a blood filter be exceeded. The present invention addresses that need by providing a blood cartridge filter that may be used and replaced without requiring the removal of the guidewire.

SUMMARY OF THE INVENTION

The present invention provides devices and methods for directing a blood filter into position using a guidewire wherein the blood filter may be deployed and replaced independently of the guidewire. More specifically, a guidewire cartridge filter system is disclosed for capturing embolic material generated during a surgical procedure within a region of interest in an artery or vein.

In accordance with the present invention, the cartridge filter system comprises an elongate member that acts as an advancing mechanism, e.g., a push wire or sheath, having a distal region attached to a filter, e.g., a parachute, basket, or scroll filter. In certain embodiments, the filter may be releasably attached to the elongate member through an interlock, which may comprise, for example, a mechanical interlock or electromechanical interlock. The filter may comprise an expansion frame and a filter material, typically a filter mesh, attached to the expansion frame. The cartridge filter system includes means for engaging the guidewire, such as a wire guide that slideably engages a guidewire. The wire guide may be attached to either or both of the elongate member and the filter. In certain embodiments, the wire guide comprises a ring having an aperture adapted to receive the guidewire. In certain other embodiments, the wire guide comprises a body portion of the elongate member having a longitudinally extending groove adapted to slideably engage the guidewire. The body portion may thus have a C-shaped cross section. Because the wire guide slideably engages the guidewire, the filter may be directed into place by the guidewire, but deployed and retracted independently of the guidewire. The filter can be placed in a collapsed condition to facilitate entry into a vessel and an expanded condition to capture embolic material in the vessel. As used herein, "advancing mechanism" denotes any elongate member or structure suitable for advancing the filter into position within a vessel while engaging the guidewire through the wire guide. The elongate member could thus be either a wire or a catheter wherein the lumen of the catheter serves as the wire guide. In one embodiment, the elongate member comprises a sheath wherein the lumen of the sheath serves as the wire guide.

Filters suitable for use within the filter system of the present invention are described, for example, in U.S. Pat. No. 5,910,154, incorporated herein by reference in its entirety. In one embodiment, the filter is biased to automatically open radially within a blood vessel. In such filters, the expansion frame may comprise a plurality of struts or arms attached to and extending distally from a distal end of the elongate member. The struts are connected to each other at each end and have an intermediate region that is biased to expand radially. Filter mesh is attached typically between the intermediate region such as the midpoint and the distal ends of the struts, thereby defining a substantially hemispherical or conical shaped filter assembly. In embodiments of the invention wherein the elongate member comprises a sheath, a filter biased to automatically open radially may be releasably carried in its collapsed condition within the sheath wherein a mechanical interlock between elongate member and the filter is formed by the friction between the filter and the lumenal wall of the sheath.

Other filters suitable for the present invention are not biased to automatically open radially within a blood vessel. In such filters, the elongate member may comprise a sheath containing an inner wire, and the expansion frame includes a plurality of struts attached to the distal end of the sheath. The struts extend distally from the sheath and attach to the distal end of the inner wire that is exposed distally beyond the sheath. At an intermediate region, the struts are notched or otherwise biased to fold out radially. Filter mesh is attached to the struts between the intermediate region and the distal end of the inner wire. With the sheath fixed, the inner wire is proximally displaced, compressing the struts and causing them to bend or buckle at the intermediate region and move radially outwardly, expanding the filter mesh across the blood vessel. As used herein, "inner wire" means any structure suitable to be slideably disposed within the sheath and stiff enough to compress the struts as the inner wire is proximally displaced with respect to the sheath. The inner wire may thus comprise an inner sheath within which the guidewire is slideably disposed.

In certain other embodiments, the filter may comprise a fluid operated filter wherein the expansion frame includes a balloon that inflates to expand the filter into an enlarged condition for use. The construction and use of expansion frames and associated filter mesh have been thoroughly discussed in earlier applications including Barbut et al., U.S. application Ser. No. 08/533,137, filed Nov. 7, 1995, Barbut et al., U.S. application Ser. No. 08/580,223, filed Dec. 28, 1995, Barbut et al., U.S. application Ser. No. 08/584,759, filed Jan. 9, 1996, Barbut et al., U.S. Pat. No. 5,769,816, Barbut et al., U.S. application Ser. No. 08/645,762, filed May 14, 1996, and Barbut et al., U.S. Pat. No. 5,662,671, and the contents of each of these prior applications are expressly incorporated herein by reference.

The methods of the present invention include prevention of distal embolization during an endovascular procedure to remove emboli and/or foreign bodies such as gas bubbles from blood vessels. The vessels include the coronary artery, aorta, common carotid artery, external and internal carotid arteries, brachiocephalic trunk, middle cerebral artery, basilar artery, subclavian artery, brachial artery, axillary artery, iliac artery, renal artery, femoral artery, popliteal artery, celiac artery, superior mesenteric artery, inferior mesenteric artery, anterior tibial artery, posterior tibial artery, and all other arteries carrying oxygenated blood. Suitable venous vessels include the superior vena cava, inferior vena cava, external and internal jugular veins, brachiocephalic vein, pulmonary artery, subclavian vein, brachial vein, axillary vein, iliac vein, renal vein, femoral vein, profunda femoris vein, great saphenous vein, portal vein, splenic vein, hepatic vein, and azygous vein.

In a method of using the cartridge filter system, the distal end of the guidewire is inserted through an artery or vein and advanced into or beyond a region of interest, typically a stenotic lesion caused by buildup of atherosclerotic plaque and/or thrombi. The guidewire may be inserted percutaneously, laparoscopically, or through an open surgical incision. In a collapsed condition, the filter and the elongate member are advanced over the guidewire, having the wire guide of the filter cartridge system engaging the guidewire. In one embodiment, the wire guide engages the elongate member at a single discrete location in a monorail fashion such as through a ring structure. If the wire guide includes a body portion of the elongate member having a longitudinally extending groove adapted to slideably engage the guidewire, the body portion engages the guidewire in an over-the-wire fashion wherein the guidewire is slideably disposed within the groove of the body portion. Alternatively, the elongate member may comprise a sheath wherein the guidewire is slideably disposed within the lumen of the sheath in an over-the-wire fashion such that the lumen serves as the wire guide. Regardless of whether the wire guide engages the guidewire in a monorail or an over-the-wire fashion, the filter is then expanded downstream of the vascular occlusion. If the wire guide engages the guidewire in an over-the-wire fashion, the elongate member may be left in the vessel during the in vivo deployment time of the filter because the elongate member and the guidewire are then integrated into a single unit, limiting the interference with further deployment of therapy devices in the vessel. If, however, the wire guide engages the guidewire in a monorail fashion, the elongate member is preferably removed from the filter during the in vivo deployment time of the filter to prevent a clinician from having to contend with the dependent movement of both the guidewire and the elongate member during the surgical procedure. Preferably, in such embodiments, the elongate member releasably attaches to the filter through a mechanical interlock. After deploying the filter, the mechanical interlock is released to allow the removal of the elongate member.

Should the in vivo deployment time of the filter be exceeded, the used filter is retracted from the body and the guidewire. If the filter and elongate member were separated by releasing an interlock, the wire guide on the elongate member must be engaged with the guidewire so that the elongate member may be displaced distally on the guidewire towards the used filter. The interlock would then be re-engaged to connect the elongate member and the used filter together whereupon the elongate member may be retracted to remove the used filter. If the elongate member and the used filter were permanently attached, the elongate member may simply be retracted to remove the used filter. An additional filter and elongate member may then be advanced over the guidewire as described herein. Because the present invention allows the removal and replacement of filters without require the removal of the guidewire, the filter system may be denoted a "cartridge filter" system in that the filter is akin to, for example, a printer cartridge, readily replaceable within the printer. After the stenotic lesion is removed or otherwise treated and an adequate lumenal diameter is established, the filter is collapsed and removed, together with the captured embolic debris, from the vessel by withdrawing another elongate member used for retrieval. Alternatively, the filter could be removed by withdrawing the guidewire to remove the entire filter system.

BRIEF DESCRIPTION OF THE DRAWINGS

FIG. 1A depicts an embodiment of an elongate member having a filter in a collapsed condition according to the present invention.

FIG. 1B depicts the elongate member of FIG. 1A having the filter in an expanded condition.

FIG. 1C depicts a cross-sectional view through section line C—C of the elongate member depicted in FIG. 1B.

FIG. 1D depicts the elongate member of FIG. 1C having a guidewire received through the wire guide.

FIG. 2A depicts an embodiment of a distal end of the guidewire.

FIG. 2B depicts an alternative embodiment of the distal end of the guidewire.

FIG. 2C depicts another alternative embodiment of the distal end of the guidewire.

FIG. 3A depicts another embodiment of the filter shaped as a parachute.

FIG. 3B depicts another embodiment of the filter shaped as an eggbeater.

FIG. 4A depicts a guidewire inserted across a vascular occlusion.

FIG. 4B depicts a monorail cartridge filter system being deployed across a vascular occlusion.

FIG. 4D depicts an over-the-wire cartridge filter system deployed across a vascular occlusion.

FIG. 5A depicts a cartridge filter system wherein the system operate as either an over-the-wire or a monorail system FIG. 5B depicts a cross-sectional view through section line B—B of the elongate member depicted in FIG. 5A.

FIG. 7C depicts the capture sheath crossing the lesion with a filter expanded downstream.

FIG. 7D depicts the guidewire and slideable filter after removal of the capture sheath and advancing mechanism.

FIG. 13A depicts another embodiment of an actuatable stop having a slideable filter bearing proximally against the stop.

FIG. 13B depicts a capture sheath disposed about and aligning the actuatable stop and filter of FIG. 13A.

FIG. 13C depicts the filter withdrawn proximally over the actuatable stop of FIG. 13B.

FIG. 14A depicts another embodiment of an actuatable stop comprising a slip stop.

FIG. 14B depicts a capture sheath disposed about and aligning the actuatable stop and filter of FIG. 14A.

DETAILED DESCRIPTION

Figure 4C:
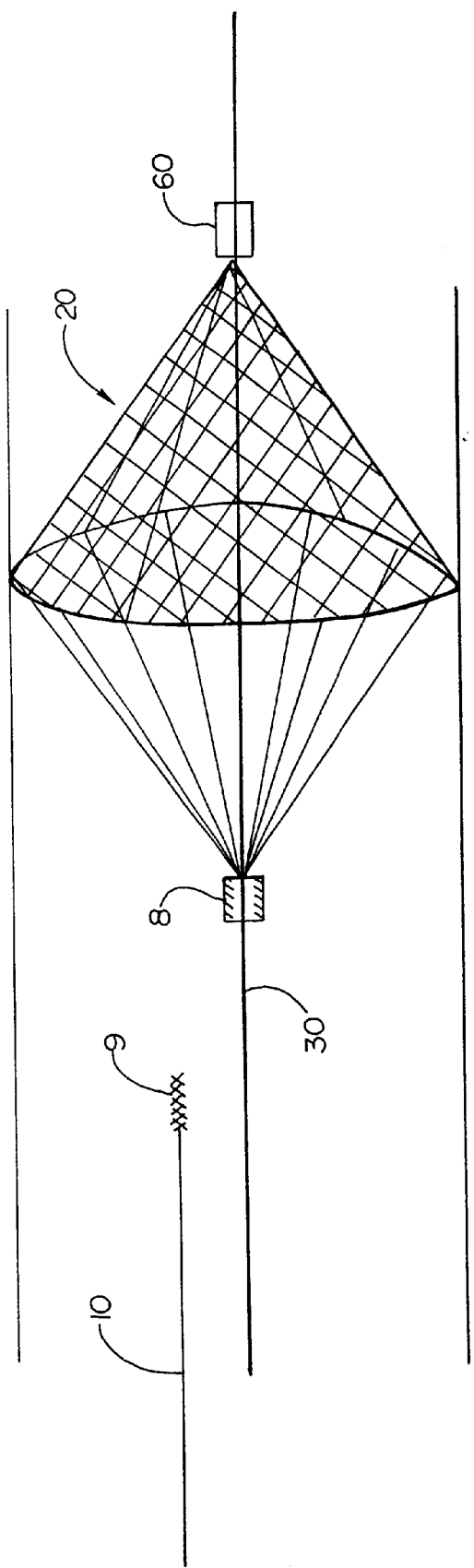
FIG. 4C depicts a monorail cartridge filter system wherein the mechanical interlock connecting the elongate member and the filter has been released.

In a first embodiment, a cartridge filter system for temporary placement in a vessel, either an artery or vein, is provided as depicted in FIGS. 1A, 1B, 1C, and 1D. The filter system includes an elongate member 10 having a proximal end, distal region 11, and expandable filter 20 mounted at the distal region. The filter 20 comprises expansion frame 22 and mesh 25 that is welded, adhesive bonded, or otherwise disposed about struts 28 of the expansion frame. Alternatively, the filter comprises a membrane extending from a proximal end to a distal end and having an expandable intermediate region. the proximal end includes segments that extend to the intermediate region and that have gaps or windows in between to allow blood to flow inside the structure. the distal end is a continuous membrane having holes drilled therein to create a filter membrane. Anticoagulants, such as heparin and heparinoids, may be applied to the mesh 25 to reduce thrombi formation. The filter 20 can be collapsed as shown in FIG. 1A to facilitate insertion into a vessel, and thereafter expanded as shown in FIG. 1B. Wire guide 26, which is adapted to slideably engage a guidewire 30, may be included in distal region 11 of the elongate member 10. Alternatively, the wire guide 26 may be integral with the filter or with both the filter and the elongate member. In certain embodiments, the wire guide 26 may comprise a ring-shaped structure. A cross-sectional view of the elongate member 10 through section line C—C is depicted in FIG. 1C. The design and construction of a variety of expandable filters suitable for use within the filter cartridge system of the present invention is described in detail in Tsugita et al., U.S. Pat. No. 5,910,154.

Figure 6:
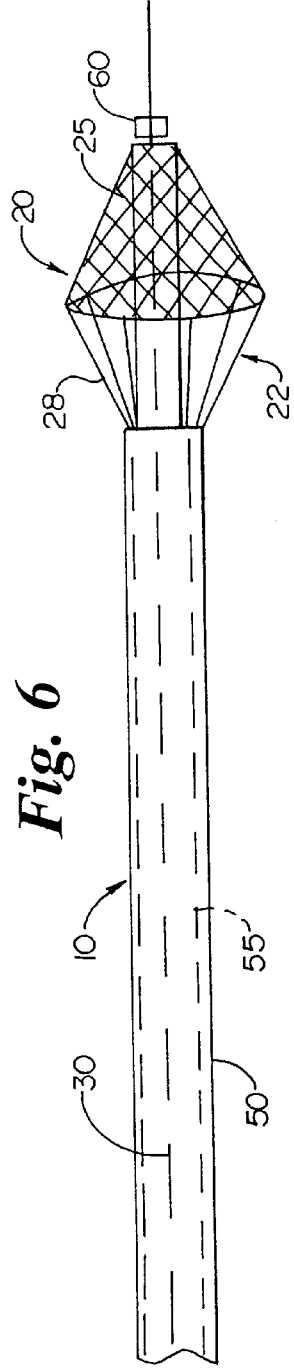
FIG. 6 depicts a cartridge filter system wherein the elongate member comprises an inner sleeve and wherein the system further includes a capture sheath.

The filter may be biased to automatically open radially within a blood vessel. In such filters, the struts of the expansion frame may be connected to each other at each end and have an intermediate region that is biased to expand radially as illustrated in FIGS. 1A and 1B. Other filters suitable for the present invention are not biased to automatically open radially within a blood vessel. One embodiment of such a filter, as illustrated in FIG. 6, the struts 28 are notched or otherwise biased to fold out radially. At a distal end of the filter, the struts attach to an inner wire 55 whereas the proximal end of the struts attach to an outer sheath 55. Proximal displacement of the inner wire 55 with respect to the outer sheath 55 causes the struts to fold out radially, thereby expanding the filter mesh 25 across a blood vessel lumen. Alternatively, the filter may be fluid operated as discussed previously.

It is to be noted that if the blood filter is biased to automatically open radially within a blood vessel, a restraint is needed to collapse the filter before it is inserted into a vessel lumen. In one embodiment, a sleeve 5 acts as the restraint to collapse the filter 20 as illustrated in FIG. 1A. To release the restraint, the sleeve 5 may be retracted from the filter 20 by proximally displacing a wire 6 as illustrated in FIG. 1B.

To deploy the cartridge filter system of the present invention, the wire guide 26 engages the guidewire 30 having a proximal end and distal end 33. The guidewire 30 is slideably received by elongate member 10 through wire guide 26 as depicted, for example, in FIG. 1D. Different constructions of the distal end 33 of the guidewire 30 are depicted in FIGS. 2A, 2B, and 2C. Distal end 33 may assume a substantially linear configuration relative to the proximal end of the guidewire as depicted in FIG. 2A. Alternatively, distal end 33 may assume an angular configuration relative to the proximal end of the guidewire as depicted in FIG. 2A. Distal end 33 may be shaped like a fishhook as depicted in FIG. 2C. The distal region of the guidewire may be constructed of a flexible material to facilitate entry through a region of interest, and preferably is equipped with an atraumatic tip as is known in the art. The embodiments in FIGS. 2B and 2C, having a curvilinear design, are particularly useful in achieving access to a complex lesion in a tortuous vessel.

FIGS. 3A and 3B depict alternative embodiments of expandable filter 20 mounted on the distal region of elongate member 10. In FIG. 3A, the filter 20 comprises an expansion frame 22 that is parachute-shaped and mesh 25 that is welded or adhesive bonded to struts 28 of the expansion frame 22. Wire guide 26 is included in the distal region of the elongate member and projects distally from filter 20 for engaging a guidewire. In FIG. 3B, filter 20 comprises an expansion frame 22 that assumes the shape of an eggbeater in its expanded state and wherein struts 28 are compressible.

By way of example, when the cartridge filter system as disclosed herein is intended for use in the aorta, the area of the mesh 25 required for the device is calculated from Bernoulli's equation as described in our earlier applications including Barbut et al., U.S. Pat. No. 5,662,671, Barbut et al., U.S. application Ser. No. 08/553,137, filed Nov. 7, 1995, Barbut et al., U.S. application Ser. No. 08/580,223, filed Dec. 28, 1995, Barbut et al., U.S. application Ser. No. 08/584,759, filed Jan. 9, 1996, Barbut et al., U.S. application Ser. No. 08/640,015, filed Apr. 30, 1996, and Barbut et al., and U.S. application Ser. No. 08/645,762, filed May 14, 1996.

The guidewire and slideable filter disclosed herein may be used in the carotid arteries, the coronary arteries, the aorta, and in where temporary filtration is desired. In an embodiment of the cartridge filter system that is to be used in the aorta, the filter material is a mesh 25 with dimensions within the following ranges is desirable: mesh area is 0.004–5 in$^2$, more preferably 0.007–4 in$^2$, more preferably 0.010–3 in$^2$, more preferably 0.015–2 in$^2$, more preferably 0.020–1 in$^2$, more preferably 0.025–0.076 in$^2$; mesh thickness is 60–280 $\mu$m, more preferably 70–270 $\mu$m, more preferably 80–260 $\mu$m, more preferably 90–250 $\mu$m, more preferably 100–250 $\mu$m, more preferably 120–230 $\mu$m, more preferably 140–210 $\mu$m; thread diameter is 30–145 $\mu$m, more preferably 40–135 $\mu$m, more preferably 50–125 $\mu$m, more preferably 60–115 $\mu$m, more preferably 70–105 $\mu$m, and pore size is 500 $\mu$m or less, more preferably 400 $\mu$m or less, more preferably 300 $\mu$m or less, more preferably 200 $\mu$m or less, more preferably 100 $\mu$m or less, more preferably 50 $\mu$m or less and usually larger than at least a red blood cell. In a preferred embodiment of the invention, mesh area is 2–8 in$^2$, mesh thickness is 60–200 $\mu$m, thread diameter is 30–100 $\mu$m, and pore size is 50–300 $\mu$m. In a further preferred embodiment of the invention, mesh area is 3–5 in$^2$, mesh thickness is 60–150 $\mu$m, thread diameter is 50–80 $\mu$m, and pore size is 100–250 $\mu$m.

In other embodiments, the filter material comprises a thin film laser cut with holes to allow blood flow (not illustrated). Typical dimensions include pore size of 20–500 $\mu$m, a thickness of 0.0005–0.003 inches, and area approximately same as for meshes described above.

Once appropriate physical characteristics are determined, suitable mesh 25 can be found among standard meshes known in the art. For example, polyester meshes may be used, such as meshes made by Saati Corporations and Tetko Inc. These are available in sheet form and can be easily cut and formed into a desired shape. In a preferred embodiment, the mesh is welded (e.g., sonic or laser) or sewn into a cone shape. Other meshes known in the art, which have the desired physical characteristics, are also suitable. Anticoagulants, such as heparin and heparinoids, may be applied to the mesh to reduce the chances of blood clotting on the mesh. Anticoagulants other than heparinoids also may be used, e.g., ReoPro (Centocor). The anticoagulant may be painted or sprayed onto the mesh. A chemical dip comprising the anticoagulant also may be used. Other methods known in the art for applying chemicals to mesh may be used.

The length of the guidewire 30 and the elongate member 10 will generally be between 30 and 300 centimeters, preferably approximately between 50 and 195 centimeters. The filter will be capable of expanding to an outer diameter of at least 0.2 centimeters, more preferably at least 0.5 centimeters, more preferably at least 1.0 centimeters, more preferably at least 1.5 centimeters, more preferably at least 2.0 centimeters, more preferably at least 2.5 centimeters, more preferably at least 3.0 centimeters, more preferably at least 3.5 centimeters, more preferably at least 4.0 centimeters, more preferably at least 4.5 centimeters, more preferably at least 5.0 centimeters. These ranges cover suitable diameters for both pediatric and adult use. The foregoing ranges are set forth solely for the purpose of illustrating typical device dimensions. The actual dimensions of a device constructed according to the principles of the present invention may obviously vary outside of the listed ranges without departing from those basic principles.

In use, as depicted in FIG. 4A, guidewire 30 may be inserted percutaneously through a peripheral artery or vein and advanced typically in the direction of blood flow. However, guidewire 30 may be inserted and advanced in a direction opposite the blood flow, e.g., retrograde through the descending aorta to reach the coronary artery. Distal end 33 of the guidewire 30 is passed through occluding lesion 100, typically an atheromatous plaque, and positioned distal to the occlusion. Elongate member 10 of FIG. 1A is inserted over the proximal end of guidewire 30 through wire guide 26, and advanced distally until filter 20 is positioned distal to plaque 100 as depicted in FIG. 4B. By having wire guide 26 engage the guidewire 30, the filter 20 and the elongate member 10 can be easily steered intravascularly to reach the region of interest. Filter 20 is expanded to capture embolic material, such as calcium, thrombi, plaque, and/or tissue debris. The useful in vivo life of filter 20 depends greatly on the type of medical procedure being performed, the condition of the patient (such as whether the patient is receiving an anticoagulant), and volume of blood flow. Although current filters can be deployed for relatively long periods (upwards of 60 minutes), it is possible that current filters will have shorter useful in vivo deployment times for the reasons noted above. Should the useful in vivo life of filter 20 be exceeded, filter 20 must be replaced by an unused filter. Unlike prior art systems in which the filter was integrated with the guidewire, in the present invention, filter 20 and elongate member 10 may be retracted from the body and guidewire 30 without requiring the removal of guidewire 30. An unused filter 20 and elongate member 10 may then be inserted over the proximal end of guidewire 30 through a wire guide 26, and advanced distally until filter 20 is positioned distal to plaque 100 similarly as depicted in FIG. 4B.

As illustrated in FIG. 4B, the wire guide 26 may engage the guidewire 30 at a single discrete location. Suitable wire guides 26 that engage the guidewire at a discrete location may comprise, for example, a ring or similar structure. Such embodiments of the cartridge filter system may be denoted "partially-threaded" or monorail systems because, proximal to the wire guide 26, the guidewire 30 and the elongate member 10 are separate and independent from one another. Other medical devices having monorail construction are known in the art. Note that proximal to the wire guide, a clinician must contend with two separate and independent structures within the vessel lumen. This can make the insertion of additional therapy devices into the vessel lumen difficult. For example, a therapy device, such as an angioplasty balloon, will typically engage the guidewire to assist positioning the therapy device in the vessel. As the therapy device is displaced along the guidewire, it may cause the elongate member to injure the vessel lumen.

To prevent such injury, the filter and elongate member may be releasably attached through an interlock in a monorail embodiment of the invention. As illustrated in FIG. 4C, the interlock may comprise a mechanical interlock having a threaded portion 9 at the distal end of the elongate member 10 adapted to engage a threaded portion 8 attached to the filter 20. After the filter 20 has been expanded to cover the vessel lumen, the elongate member 10 is rotated to release the mechanical interlock by unthreading the threaded portions 8 and 9. Note that the filter 20 is then retained only by the guidewire 30. To assist the retention of the filter 20 along the guidewire, the guidewire may have a stop 60 to prevent further distal displacement of the filter. In such an embodiment, the filter is free, however, to displace proximally. The pressure from the blood flow and the tension provided by the expansion of the filter against the walls of the vessel lumen will tend to prevent proximal displacement. Although such forces will tend to prevent proximal displacement, it may be beneficial during some procedures to allow a small amount of proximal displacement when necessary.

As used herein, "elongate member" denotes any structure suitable for advancing filter 20 into position within a vessel while engaging guidewire 30 through a wire guide 26. Thus elongate member 10 may comprise, of course, a wire. Alternatively, elongate member 10 may comprise a catheter such as a balloon catheter suitable for angioplasty. If elongate member 10 comprises a catheter, the lumen of the catheter may serve as the wire guide 26. In such an embodiment, elongate member 10 slideably engages guidewire 30 in an "over-the-wire" manner similar to, for example, the manner in which a single lumen catheter is threaded over a guidewire in neuroradiological procedures. Turning now to FIG. 4D, an over-the-wire cartridge filter system is illustrated. Elongate member 10 comprises a catheter or sleeve 35 wherein the lunmen 40 of the catheter 35 serves as the wire guide 26. The expansion frame 22 of filter 20 attaches to the catheter 35 along the catheter wall portion 42. Unlike the monorail system illustrated in FIG. 4B, a clinician threading additional devices into the blood vessel in which an over-the-wire cartridge filter system is deployed will not have to contend with two independent structures within the blood vessel lumen. Inspection of the monorail cartridge filter system illustrated in FIG. 4B reveals that proximal to the filter 20, the guidewire 30 and elongate member 10 are independent of one another, potentially hampering the deployment of additional devices within the blood vessel. Nevertheless, monorail or partially-threaded systems possess advantages over an over-the-wire system (that may be denoted as "fully-threaded"). For example, in angioplasty procedures or the like, the guidewire 30 must be relatively long to extend from vessels within a patient's leg to the heart. If the proximal portion of the guidewire 30 that extends outside the patient's body is relatively short, there comes a point at which, as the elongate member 10 is retracted from the body, the elongate member 10 will entirely cover this external proximal portion of the guidewire 30 (in an over-the-wire cartridge filter system). The clinician would then no longer be able to maintain the position of the guidewire 30. Thus, as is known in other medical procedures, over-the-wire medical devices require relatively long proximal transfer portions external to a patient's body, causing inconvenience during catheterization procedures.

The present invention includes over-the-wire filter cartridge system embodiments that do not require the relatively long proximal transfer portions of prior art over-the-wire systems. For example, in FIGS. 5A and 5B, an embodiment of such a filter cartridge system is illustrated. Elongate member 10 may include a ring-shaped wire guide 26 that attaches to the expansion frame 22 of filter 20 (filter 20 only partly illustrated). Elongate member 10 also includes a body portion 46 having a longitudinally extending groove 45 adapted to slideably engage wire guide 30. In one embodiment, groove 45 is shaped such that body portion 46 has a C-shaped cross section as illustrated in FIG. 5B. The elongate member 10 is constructed of a suitably flexible material such that a clinician may force guidewire 30 into the groove 46 by forcing apart arms 47 and 48 of the "C" formed by groove 46. The guidewire 30 would then be held within groove 46 by arms 47 and 48. Outside the body, the elongate member 10 and the guidewire 30 may be kept separate, eliminating the need for a long proximal transfer portion outside the patient's body. Within a vessel, however, the system of FIGS. 5A and 5B will operate as an over-the-wire system. As the filter 20 and elongate member 10 are retracted from the guidewire 30 and the patient's body, the guidewire 30 may be separated from the elongate member 10 by pulling apart the already separated portions of elongate member 10 and guidewire 30. The resulting tension flexes arms 47 and 48 outwardly, allowing the guidewire 30 to be removed from the groove 45.

Although the groove 45 slideably engages the guidewire 30, it is to be noted that (particularly when body portion 46 has a C-shaped cross section) the guidewire 30 may not be entirely circumferentially surrounded by elongate member 10 as is the case in ordinary over-the-wire systems (such as illustrated in FIG. 4c). To provide full circumferential support around guidewire 30, elongate member 10 may have one or more spiral portions 47 wherein the elongate member spirals about guidewire 30 such that spiral portion 47 resembles coils of a spring. Note that should the elongate member 10 include the spiral portions 47, as the filter 20 and elongate member 10 are retracted from the guidewire 30, the clinician will unravel the spring portion 47 to separate it from the guidewire 30. Conversely, as the elongate member 10 is being advanced along guidewire 30, the clinician must ravel spiral portion 47 about the guidewire 30 to continue deployment of a filter.

Regardless of whether the cartridge system is an over-the-wire or a monorail system, one of ordinary skill in the art will appreciate that there are a number of ways to actuate the filter of the present invention. For example, if the filter is biased to automatically open radially within a blood vessel, the cartridge filter system may be contained within a catheter or sheath 5 as illustrated in FIG. 1A. As the elongate member and filter are advanced beyond the sheath 5, the filter will automatically expand radially within the vessel because of the pre-existing bias within the filter as illustrated in FIG. 1B. Alternatively, the filter may be fluid operated wherein the filter contains a balloon that expands to expand the filter. In addition, the filter may be mechanically actuated by the clinician.

Turning now to FIG. 6, a mechanically actuated cartridge filter system is illustrated. In such filters, the elongate member 10 may comprise a sheath or catheter 50 containing an inner wire 55 wherein the expansion frame 22 includes a plurality of struts 28 attached to the distal end of the sheath 50. The struts 28 extend distally from the sheath 50 and attach to the distal end of the inner wire 55 that is distally exposed beyond the sheath. At an intermediate region, the struts 28 are notched or otherwise biased to fold out radially. Filter mesh 25 is attached to the struts 28 between the intermediate region and the distal end of the inner sheath 55. To open the filter 20, the sheath 50 is fixed in position, and the inner wire 55 is proximally displaced, compressing the struts 28 and causing them to bend or buckle at the intermediate region and move radially outwardly, expanding the filter mesh 25 across the blood vessel. It is to be noted that the guidewire 30 may have a stop 60 formed to assist the positioning and deployment of the filter 20 along the guidewire 30.

As used herein, "inner wire" means any structure suitable to be slideably disposed within the sheath 50 and stiff enough to compress the struts 28 as the inner wire 55 is proximally displaced with respect to the sheath 50. Thus, as illustrated in FIG. 6, the inner wire 55 may comprise an inner sheath 55 that slideably contains the guidewire 30 within a lumen of the inner sheath. Note that the inner sheath 55 and the sheath 50 may each possess a body portion having a longitudinally extending slit therein (not illustrated). Within both the inner sheath 55 and the sheath 50, the combination of the slit and the lumen would therefore comprise the longitudinally extending groove already described. Therefore, the cartridge filter system illustrated in FIG. 6 could be advanced within a blood vessel in an over-the-wire fashion yet not require a relatively long proximal transfer portion as described with respect to the embodiment of the cartridge filter system illustrated in FIGS. 5A and 5B.

Figure 7A:
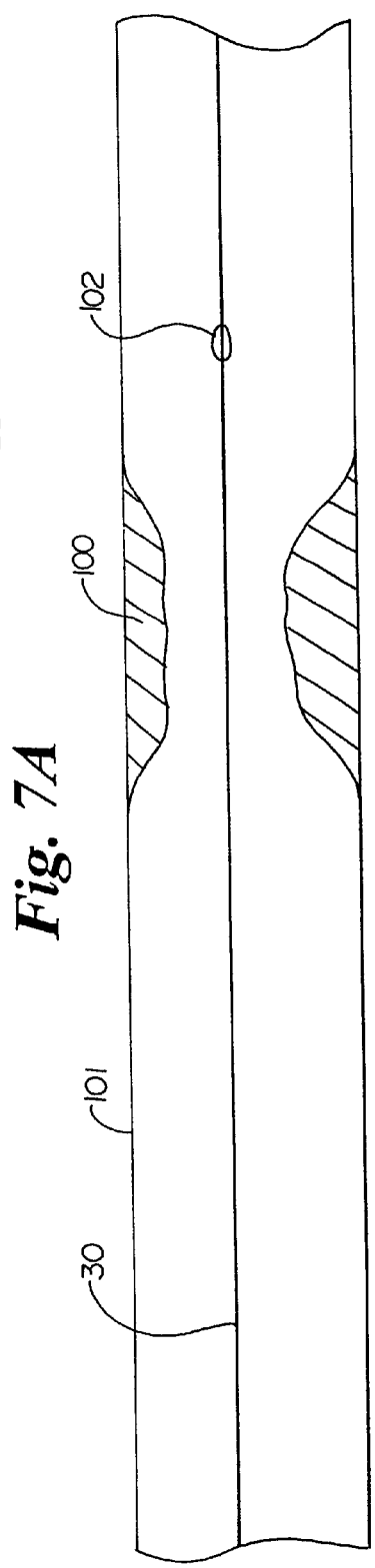
FIG. 7A depicts a guidewire with a distal stop positioned across a vascular lesion.
Figure 7B:
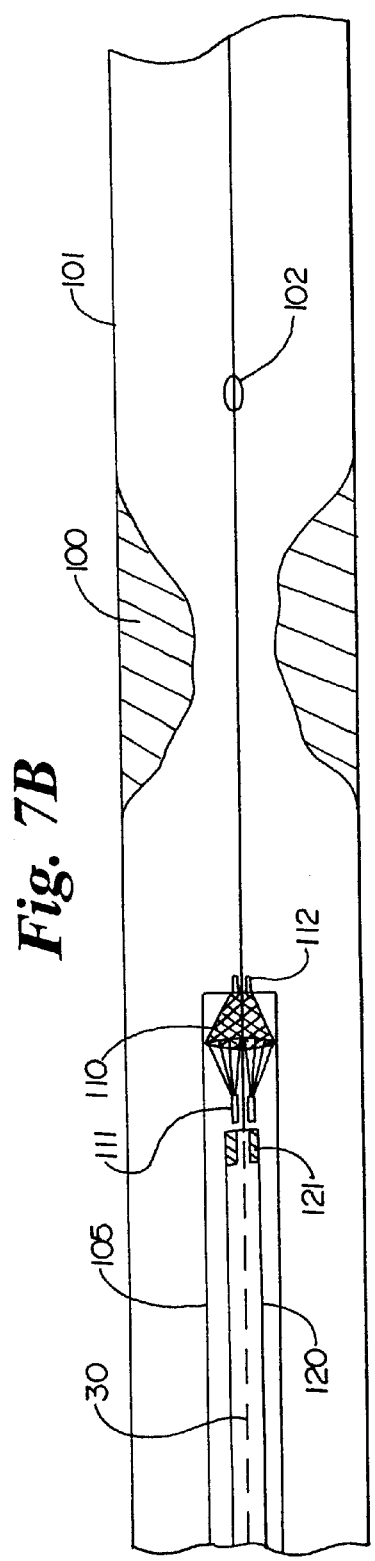
FIG. 7B depicts a slideable filter, an advancing mechanism, and a capture sheath disposed over the guidewire of FIG. 7A.

Another method for deploying a slideable filter along a guidewire is shown in FIGS. 7A–7D. According to this method, guidewire 30 is first positioned across lesion 100 within vessel 101. Guidewire 30 may include a distal stop 102. Filter 110, having proximal end 111 and distal end 112, is then advanced along guidewire 30. This step of advancement is typically performed with capture sheath 105 disposed about filter 110. Advancement may also be accomplished using an advancing mechanism 120 having distal end 121 that bears against proximal end 111 of filter 110. Alternatively, the static friction between filter 110 and sheath 105 may be adequate to advance the filter along guidewire 30, in which case sheath 105 is the advancing mechanism. Once filter 110 is positioned downstream of lesion 100, capture sheath 105 is withdrawn, allowing the filter to expand as depicted in FIG. 7C. Further distal advancement of filter 110 is prohibited by frictional engagement of filter 110 by the vessel lumen or by stop 102 when present. Alternatively, filter 110 may be equipped with an actuatable locking mechanism that engages guidewire 30 when the filter is properly positioned. After expansion of filter 110, capture sheath 105 and advancing mechanism 120 are withdrawn from the region of interest as shown in FIG. 7D, and removed from the patient's vessel.

Figure 8:
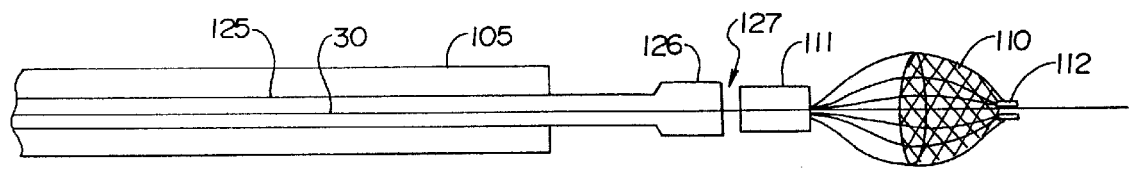
FIG. 8 depicts an advancing mechanism connected to a slideable filter through a flush contact.
Figure 9A:
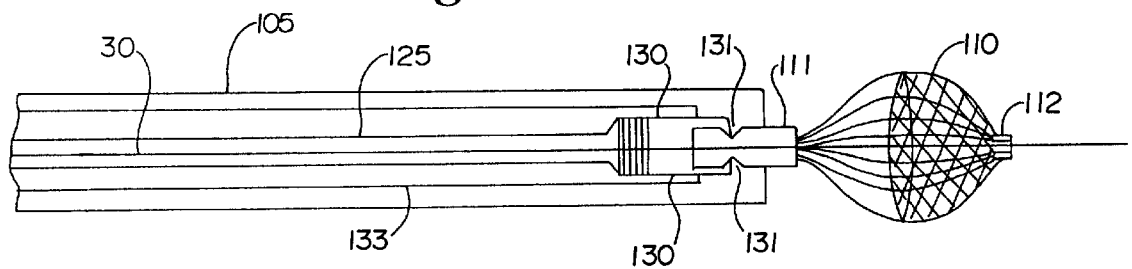
FIG. 9A depicts an advancing mechanism connected to a slideable filter through pivoting claws.
Figure 9B:
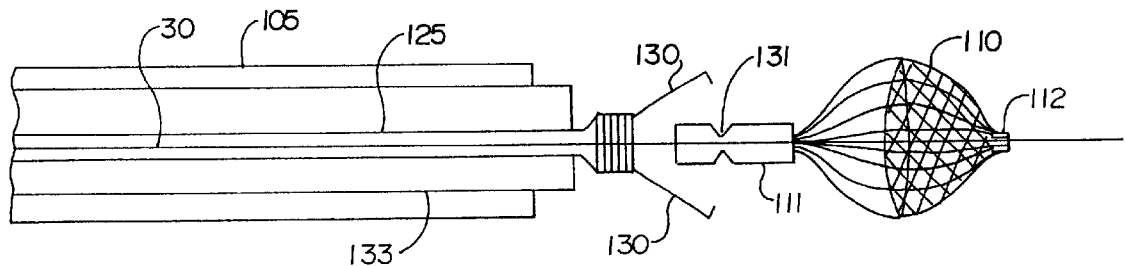
FIG. 9B depicts the opening of the pivoting claws of FIG. 9A.

In certain embodiments, the advancing mechanism bears against proximal end 111 of filter 110, but is not otherwise connected. In other embodiments as shown in FIG. 8, advancing mechanism 125, having distal end 126, is coupled through flush contact interlock 127 to proximal end 111 of filter 110. In this case, the interlock is activated by magnetic or electromagnetic force and is releasable. FIGS. 9A and 9B show an alternative mechanical interlock. In FIG. 9A, pivoting claws 130 are mounted at the distal end of advancing mechanism 125. The distal end of each claw 130 is adapted to engage recess 131 disposed circumferentially about proximal end 111 of filter 110. Claws 130 are maintained in contact with recess 131 by the action of locking sheath 133 that bears circumferentially against claws 130. When capture sheath 105 and locking sheath 133 are withdrawn as depicted in FIG. 9B, claws 130 pivot out of engagement, thereby releasing filter 110.

Figure 10A:
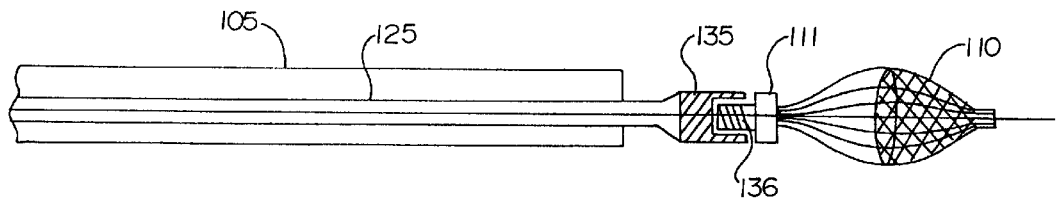
FIG. 10A depicts an advancing mechanism connected to a slideable filter through a threaded interlock.
Figure 10B:
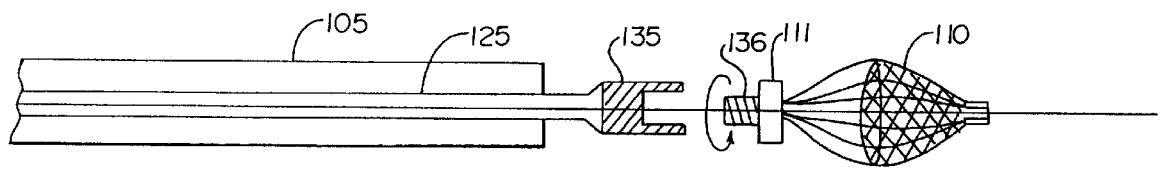
FIG. 10B depicts the opening of the threaded interlock of FIG. 10A.

Another mechanical interlock is shown in FIGS. 10A and 10B. FIG. 10A shows a threaded interlock between threaded screw 136 mounted on proximal end 111 of filter 110. The screw engages coupling 135 having a threaded portion adapted to receive screw 136. FIG. 10B depicts disengagement of coupling 135 from screw 136 to permit removal of advancing mechanism 125 and capture sheath 105 from the patient's vessel. In order to disengage the coupling from the screw it may be necessary to have a rotational lock on the filter, so that the coupling can be rotated while the filter remains fixed.

Figure 11A:
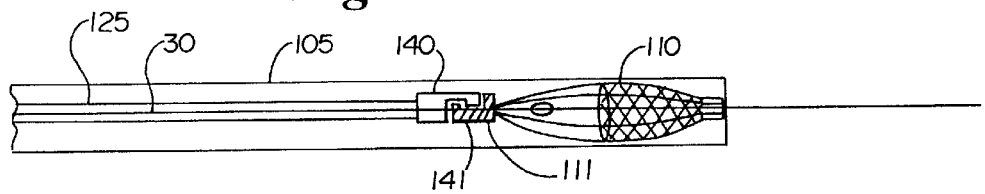
FIG. 11A depicts the slideable filter connected to an advancing mechanism through a mechanical interlock.
Figure 11B:
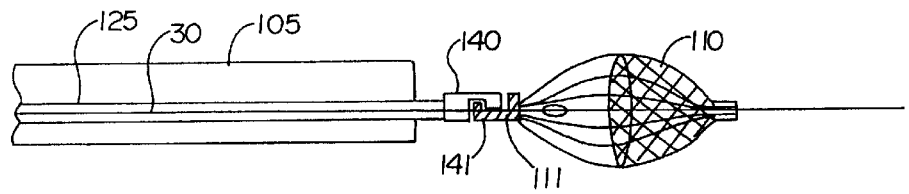
FIG. 11B depicts the assembly of FIG. 11A after removal of a capture sheath.
Figure 11C:
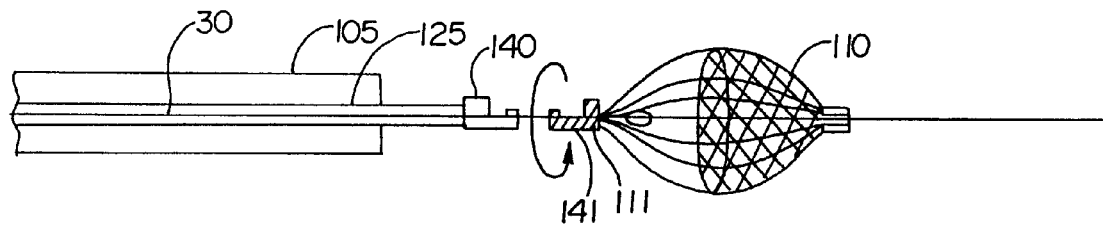
FIG. 11C depicts the assembly of FIG. 11B after rotation of the mechanical interlock.
Figure 11D:
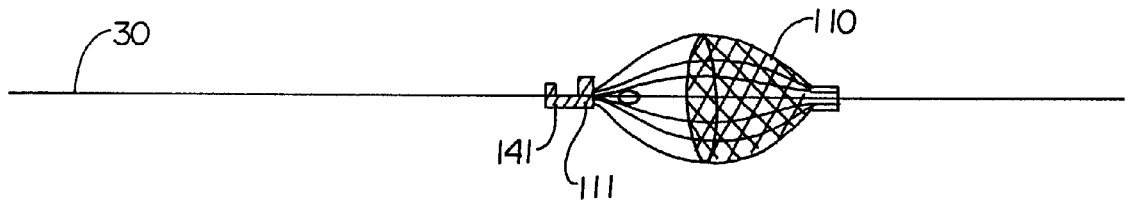
FIG. 11D depicts the assembly of FIG. 11C after removal of the sheath and advancing mechanism.

A further mechanical interlock is shown in FIGS. 11A–11D. FIG. 11A shows first hook 140 mounted at the distal end of advancing mechanism 125. Second hook 141 is mounted at proximal end 111 of filter 110, and is adapted to engage first hook 140. Engagement of hooks 140 and 141 is dependent upon proper rotational alignment of the hooks. This alignment is maintained so long as sheath 105 surrounds the interlock. FIG. 11B shows the interlock after placement within a vessel and removal of sheath 105. As depicted in FIG. 11C rotation of hook 140 disengages the interlock. Advancing mechanism 125 and sheath 105 are then removed from the region of interest and from the patient's vessel as shown in FIG. 11D. In addition to the detachable interlock mechanisms discussed above, a number of additional mechanisms have been disclosed in U.S. Pat. Nos. 5,312,415, 5,108,407, 5,891,130, 5,250,071, 5,925,059, 5,800,455, 5,800,543, 5,725,546, 5,350,397, 5,690,671, 5,944,733, 5,814,062, and 5,669,905, all of which are expressly incorporated herein by reference in their entirety. It will understood that any of the interlocks disclosed in any of these patents may be used in the present invention.

Figure 12A:
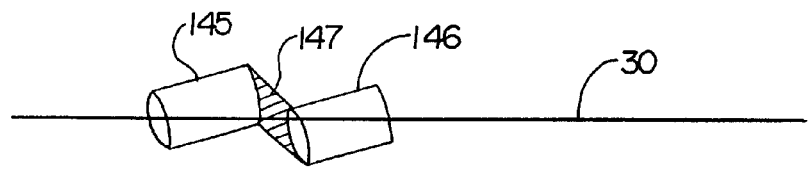
FIG. 12A depicts an actuatable stop comprising off-center tubes disposed along a guidewire.
Figure 12B:
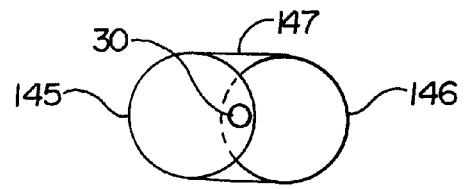
FIG. 12B depicts a distal view of the stop of FIG. 12A.
Figure 12C:
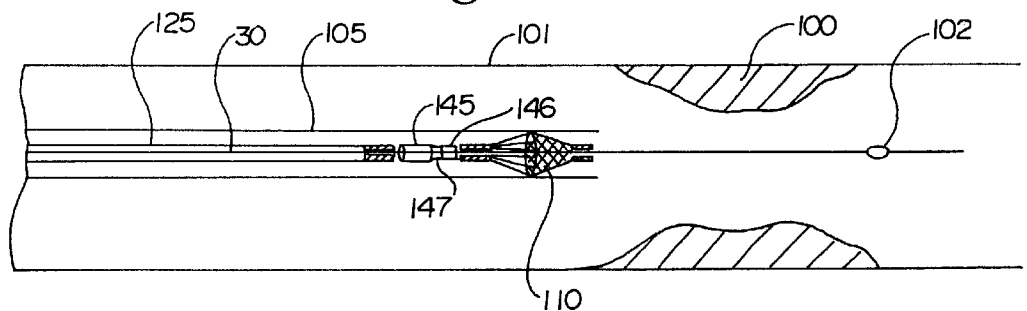
FIG. 12C depicts insertion of a slideable filter and the stop of FIG. 12A into a vessel.
Figure 12D:
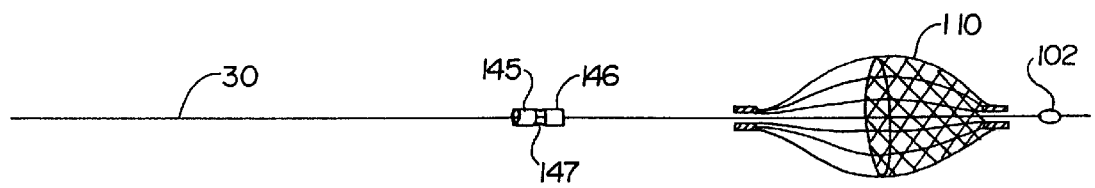
FIG. 12D depicts the slideable filter and stop of FIG. 12C after removal of the capture sleeve.
Figure 12E:
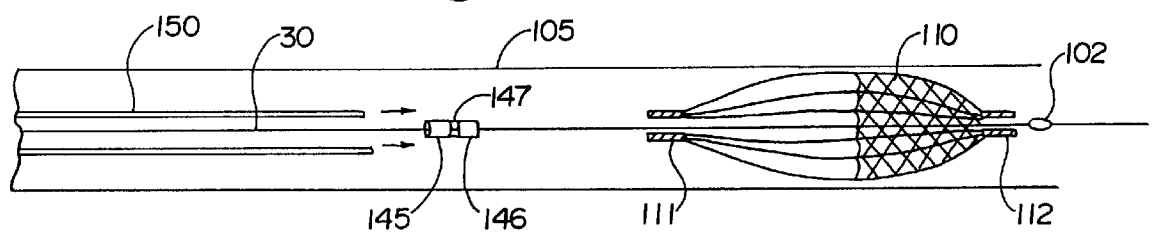
FIG. 12E depicts the slideable filter and stop of FIG. 12C before advancement of the alignment sheath.

As noted above, one or more distal and/or proximal stops may be placed along the guidewire. These stops may be pre-mounted, installed during a procedure, or integral with the filter and simultaneously inserted therewith. An actuatable stop is shown in FIGS. 12A–12E. Referring to FIG. 12A, the proximal stop is comprised of off-centered tubes, shown here as first tube 145, second tube 146, and biasing element 147 connecting the first and second tubes. When misaligned as shown in FIG. 12A, first and second tubes 145 and 146, respectively, pinch and frictionally engage guidewire 30 as shown in FIG. 12B. In use, this slideable stop can be employed proximal of the filter as shown in FIG. 12C. Sheath 105 contains advancing mechanism 125, an actuatable stop including first and second tubes 145 and 146 coupled through biasing element 147, and filter 110. Sheath 105 forces first and second tubes 145 and 146 into near coaxial alignment, thereby permitting the stop to slide over guidewire 30. This assembly is advanced across lesion 100 until the filter reaches optional distal stop 102. The filter and proximal stop are then released from sheath 105 as depicted in FIG. 12D, the stop engaging the guidewire. Sheath 105 and advancing mechanism 125 are then removed from the patient's vessel. After performance of an endoluminal procedure (e.g., angioplasty, stent deployment, angiography, atherectomy), the filter and stop are retrieved by sheath 150 as depicted in FIG. 12E. Sheath 150 first captures first and second tubes of the stop and forces them into alignment against the action of biasing element 147. In this manner, the stop is deactuated and again slides over guidewire 30. Sheath 150 then captures filter 110 that bears against optional stop 102 during advancement of sheath 150 over filter 110. The entire assembly, including sheath 150, filter 110, and the proximal stop, are then removed from the patient's vessel.

In another embodiment, a pivoting proximal stop is used as shown in FIGS. 13A–13C. Referring to FIG. 13A, the proximal stop is comprised of tapered proximal section 156 and flat distal section 155, the tapered proximal section allowing a filter to pass distally when advanced over the stop. Proximal section 156 has lumen 157 adapted to receive guidewire 30. Section 155 lies in a plane substantially perpendicular to the axis of lumen 157. In this manner, the proximal stop pivots and frictionally engages guidewire 30 when proximal end 111 of filter 110 bears against section 155. Filter 110 is retrieved and withdrawn over the stop as shown in FIG. 13B. Sheath 105, optionally a stepped sheath as depicted in FIG. 15B, aligns the stop with the opening at the proximal end 111 of filter 110, permitting the filter to pass proximally over the stop as shown in FIG. 13C.

In another embodiment, a slip stop is used as the proximal stop as depicted in FIGS. 14A and 14B. Slip stop 160 comprises a tubular segment having open distal end 162 and tapered proximal end 161. Guidewire 30 passes smoothly through proximal end 161 when distal end 162 is centered about guidewire 30. However, when stop 160 becomes misaligned, as shown in FIG. 14A, proximal end 161 pinches and frictionally engages guidewire 30, preventing proximal advancement of filter 110. To retrieve filter 110, sheath 105, optionally a stepped sheath as shown, is advanced distally over stop 160 and filter 110, thereby aligning slip stop 160 with the opening at proximal end 111 of filter 110, as shown in FIG. 14B.

Figure 15A:
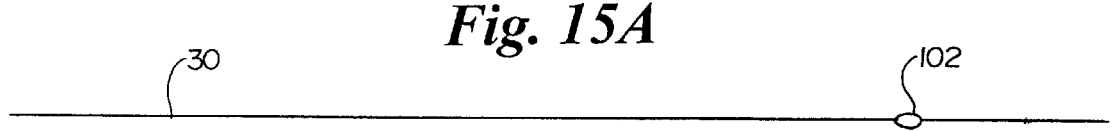
FIG. 15A depicts a guidewire having a single distal stop.
Figure 15B:
FIG. 15B depicts a guidewire having proximal and distal stops, wherein the stops are pivoting barbs.
Figure 15C:
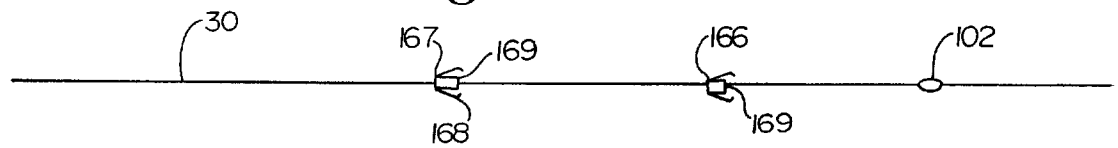
FIG. 15C depicts a guidewire having a distal stop and two proximal stops, wherein the proximal stops comprise pivoting cleats.
Figure 15D:
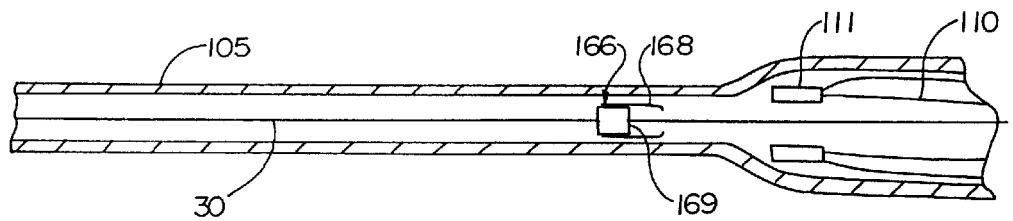
FIG. 15D depicts a capture sheath disposed about and aligning the cleats with a filter.
Figure 15E:
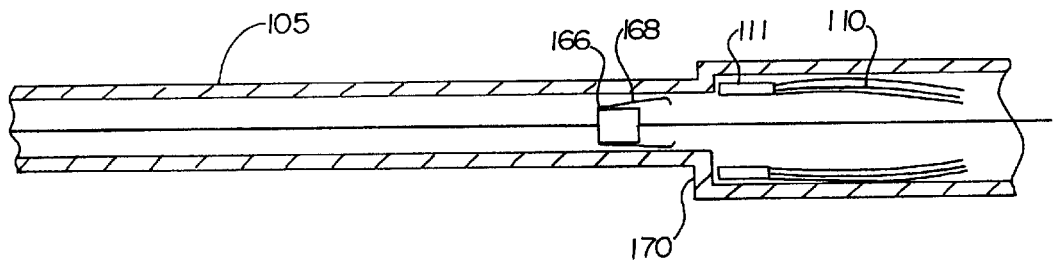
FIG. 15E depicts another embodiment of a capture sheath disposed about and aligning the cleats with a filter.

FIG. 15A shows a guidewire having one distal stop 102. FIG. 15B shows a guidewire having distal stop 102 and proximal stop 165. Proximal stop 165 may be mounted on a pivot about its mid-point, thereby allowing a filter to pass proximal to distal, and later be retrieved distal to proximal, provided sufficient force is applied to pivot the stop. FIG. 15C shows two proximal stops 166 and 167, each comprising a plurality of pivoting cleats 168 attached to housing 169 that engages guidewire 30. It will understood that any number of proximal and distal stops may be employed, including 1, 2, 3, 4, 5, 6, 7, or any other desired number depending on the procedure. FIG. 15D shows retrieval of filter 110. Sheath 105 restrains cleats 168 to allow passage of proximal end 111 of filter 110 over the cleats. In certain embodiments, it may be desirable for sheath 105 to include a sharp step, shown as numeral 170 in FIG. 15E. This sheath will maintain closure of cleats 168 until the cleats are guided within proximal end 111 of filter 110, permitting removal of the filter over the cleats.

Figure 16A:
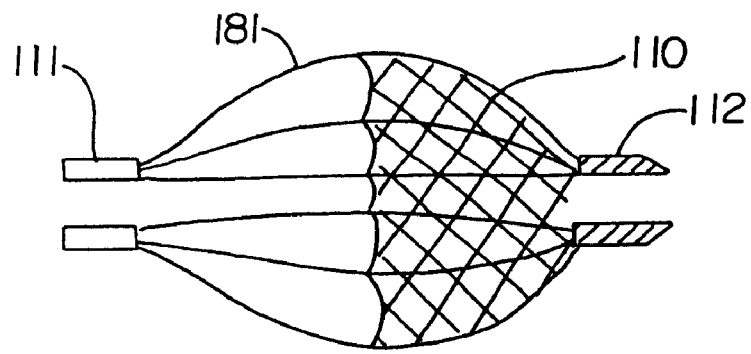
FIG. 16A depicts an open carriage filter structure.
Figure 16B:
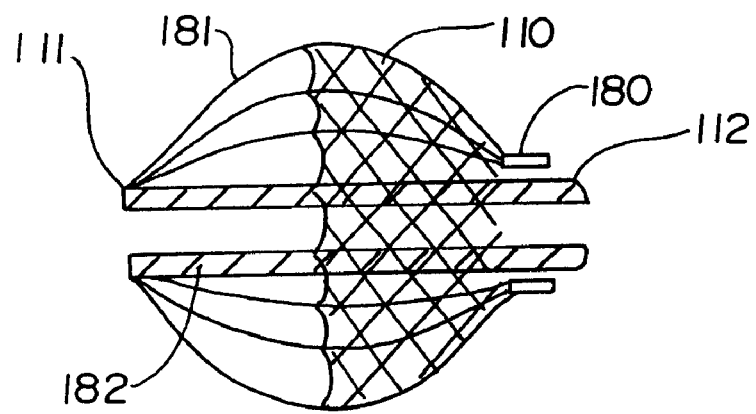
FIG. 16B depicts a continuous carriage filter structure.

The sliding filter as disclosed herein may be constructed with an open carriage as shown in FIG. 16A or a continuous carriage as shown in FIG. 16B. Referring to FIG. 16A, a plurality of struts 181 join proximal end 111 to distal end 112. Filter 110 is disposed about a portion of struts 181, either over or under the struts. Struts 181 buckle radially outward when proximal end 111 and distal end 112 are forced together. In certain embodiments, distal end 112 will include a tapered edge as shown in FIG. 16A. FIG. 16B depicts a continuous carriage extending from proximal end 111 to distal end 112, and terminating in a tapered distal edge. Sliding ring 180 may be incorporated distal or proximal. Struts 181 are connected at a first end to carriage 182 and at a second end to sliding ring 180. Struts 181 buckle radially outward when sliding ring 180 and carriage 182 are forced together.

Although the foregoing invention has, for the purposes of clarity and understanding, been described in some detail by way of illustration and example, it will be obvious that certain changes and modifications may be practiced that will still fall within the scope of the appended claims. Moreover, it will be understood that each and every feature described for any given embodiment or in any reference incorporated herein, can be combined with any of the other embodiments described herein.

What is claimed is:

1. A medical device comprising:
    a guidewire having a proximal end and a distal end;
    a delivery sheath having a proximal end, a distal end, and a lumen therebetween, the delivery sheath slideably engaging the guidewire;
    a filter releasably carried within the lumen of the delivery sheath, the filter slideably engaging the guidewire and removable from the guidewire by sliding the filter proximally on the guidewire; and
    a first and second stop, the first stop disposed proximally of the filter and the second stop disposed distally of the filter, wherein the first stop is attachable to the guidewire at or near the proximal end of the filter, and The first stop is slideable along the guidewire, and wherein the second stop is secured to the guidewire;
    wherein, in use, the guidewire is positioned within a vessel of a patient, the filter and delivery sheath are advanced along the guidewire to a region of interest within the vessel, and the delivery sheath is removed from the filter to release the filter.

2. The medical device of claim 1, further comprising an endoluminal therapeutic catheter.

3. The medical device of claim 2, wherein the endoluminal therapeutic catheter is an angioplasty catheter.

4. A method for protecting a patient during an endoluminal procedure, comprising the steps of:
    advancing a guidewire to a region of interest within a vessel;
    advancing a filter and delivery sheath along the guidewire, the filter carried by the delivery sheath;
    removing the delivery sheath from the filter, thereby releasing the filter;
    expanding the filter within the region of interest;
    removing the delivery sheath from the region of interest;
    advancing a catheter over the guidewire to the region of interest;
    performing an endoluminal procedure at the region of interest, wherein released embolic material is captured by the filter;
    removing the catheter from the region of interest;
    advancing a capture sheath over the guidewire;
    engaging the filter with the capture sheath; and
    removing the filter and capture sheath from the region of interest.

5. The medical device of claim 1, wherein said first stop includes a biasing mechanism.

6. The medical device of claim 5, wherein said biasing mechanism comprises a plurality of tubes coupled to a biasing element, said plurality of tubes adapted to fictionally engage the guidewire.

7. The medical device of claim 5, further comprising a means for actuating said biasing mechanism to the guidewire.

8. The medical device of claim 1, wherein said first stop comprises a tapered proximal section defining a lumen adapted to receive The guidewire, and a flat distal section which lies in a plane substantially perpendicular to the axis of said lunen, wherein said tapered proximal and flat sections are adapted to frictionally engage the guidewire.

9. The medical device of claim 1, wherein said fist stop includes a slip stop.

10. The medical device of claim 9, wherein said slip stop comprises a tubular segment having an open distal end and a tapered proximal end, said tapered proximal end adapted to frictionally engage the guidewire.

* * * * *

UNITED STATES PATENT AND TRADEMARK OFFICE
CERTIFICATE OF CORRECTION

PATENT NO.    : 6,371,971 B1
DATED         : April 16, 2002
INVENTOR(S)   : Tsugita et al.

It is certified that error appears in the above-identified patent and that said Letters Patent is hereby corrected as shown below:

<u>Column 16,</u>
Line 1, cancel beginning with "4. A method for protecting" to and including "interest;" in line 23.

Signed and Sealed this

Twenty-ninth Day of July, 2003

JAMES E. ROGAN
*Director of the United States Patent and Trademark Office*